(12) United States Patent
Miller et al.

(10) Patent No.: US 10,788,458 B2
(45) Date of Patent: *Sep. 29, 2020

(54) DETECTION OF BLOCKAGE IN A POROUS MEMBER

(71) Applicant: MSA TECHNOLOGY, LLC, Cranberry Township, PA (US)

(72) Inventors: Jerin Miller, Pittsburgh, PA (US); Ryan Alan Sherry, Cranberry Township, PA (US); Robert Kevin Sexton, Butler, PA (US); Robert Eric Uber, Pittsburgh, PA (US)

(73) Assignee: MSA Technology, LLC, Cranberry Township, PA (US)

( * ) Notice: Subject to any disclaimer, the term of this patent is extended or adjusted under 35 U.S.C. 154(b) by 484 days.

This patent is subject to a terminal disclaimer.

(21) Appl. No.: 15/394,566

(22) Filed: Dec. 29, 2016

(65) Prior Publication Data

US 2017/0227499 A1 Aug. 10, 2017

Related U.S. Application Data

(60) Provisional application No. 62/291,823, filed on Feb. 5, 2016.

(51) Int. Cl.
| | |
|---|---|
| *G01N 29/04* | (2006.01) |
| *G01N 29/07* | (2006.01) |
| *G01N 29/34* | (2006.01) |
| *G01N 29/11* | (2006.01) |
| *G01N 33/00* | (2006.01) |
| *G01N 21/17* | (2006.01) |

(52) U.S. Cl.
CPC .......... *G01N 29/04* (2013.01); *G01N 29/075* (2013.01); *G01N 29/11* (2013.01); *G01N 29/348* (2013.01); *G01N 33/007* (2013.01); *G01N 21/1702* (2013.01); *G01N 2291/0289* (2013.01)

(58) Field of Classification Search
CPC ......... G01N 33/007; G01N 2291/0289; G01N 29/04; G01N 33/0006; G01N 21/1702
See application file for complete search history.

(56) References Cited

U.S. PATENT DOCUMENTS

| | | | |
|---|---|---|---|
| 5,753,797 A | * | 5/1998 | Forster ............... G01N 21/1702 250/343 |
| 7,034,943 B1 | | 4/2006 | Moeckli |
| 7,242,479 B2 | | 7/2007 | Moeckli |
| 7,318,335 B2 | | 1/2008 | Olesen |

(Continued)

FOREIGN PATENT DOCUMENTS

| | | |
|---|---|---|
| EP | 2104078 A2 | 9/2009 |
| EP | 2189956 A1 | 5/2010 |

(Continued)

*Primary Examiner* — Dennis White
*Assistant Examiner* — Bryan Kilpatrick
(74) *Attorney, Agent, or Firm* — Bartony & Associates LLC

(57) ABSTRACT

A method of detecting at least a partial blockage in a porous member separating an inner chamber of a device having a gas sensor responsive to an analyte positioned within the inner chamber and an ambient environment includes emitting pressure waves within the inner chamber and measuring a change in phase of a response via a sensor responsive to pressure waves.

18 Claims, 25 Drawing Sheets

(56) References Cited

U.S. PATENT DOCUMENTS

| | | |
|---|---|---|
| 7,413,645 B2 | 8/2008 | Scheffler |
| 7,791,475 B2 | 9/2010 | Clow |
| 7,886,576 B2 | 2/2011 | Uber |
| 7,959,777 B2 | 6/2011 | Scheffler |
| 2008/0252891 A1* | 10/2008 | Uber .................. G01N 21/1702 356/437 |
| 2009/0267755 A1 | 10/2009 | Ropke |
| 2013/0047703 A1 | 2/2013 | Stengel |
| 2013/0186776 A1 | 7/2013 | Scheffler |
| 2013/0186777 A1 | 7/2013 | Scheffler |
| 2013/0192332 A1 | 8/2013 | Scheffler |
| 2013/0193004 A1 | 8/2013 | Scheffler |
| 2014/0273263 A1 | 9/2014 | Zanella, Sr. |
| 2016/0320361 A1 | 11/2016 | Johansen |
| 2017/0219515 A1 | 8/2017 | Davis |
| 2017/0227498 A1* | 8/2017 | Miller .................... G01N 29/04 |

FOREIGN PATENT DOCUMENTS

| | | |
|---|---|---|
| JP | 02128298 | 5/1990 |
| WO | WO2017136559 | 8/2017 |

\* cited by examiner

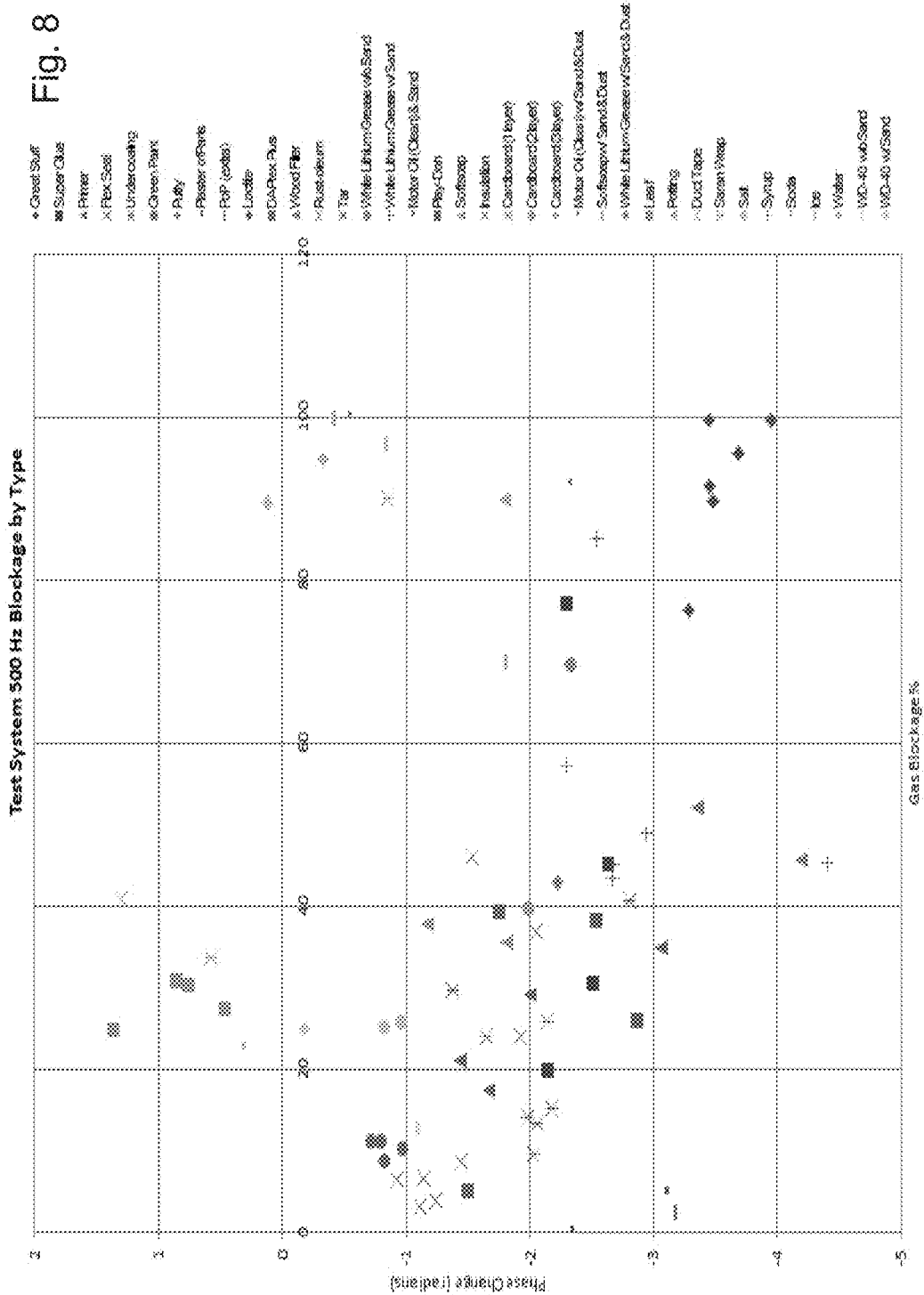

Fig. 9F
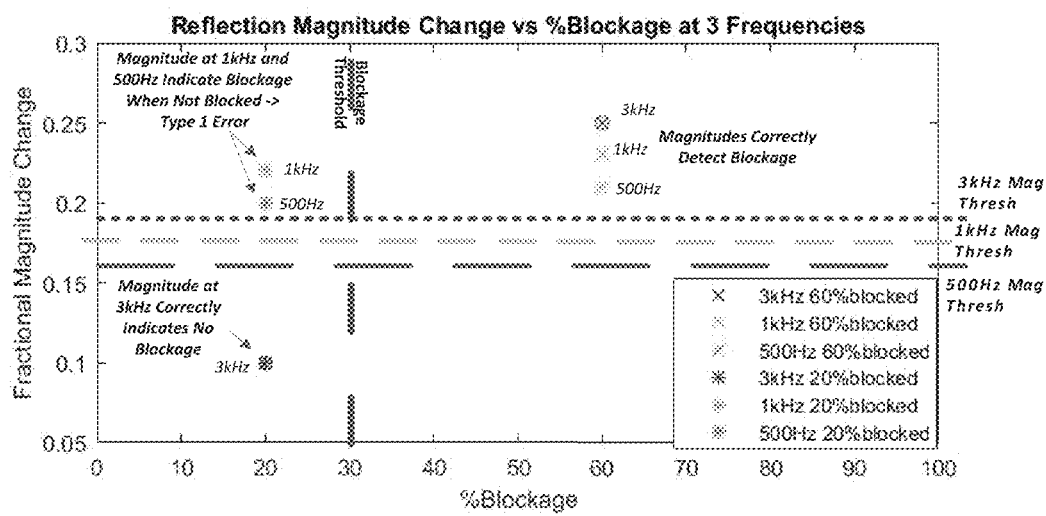
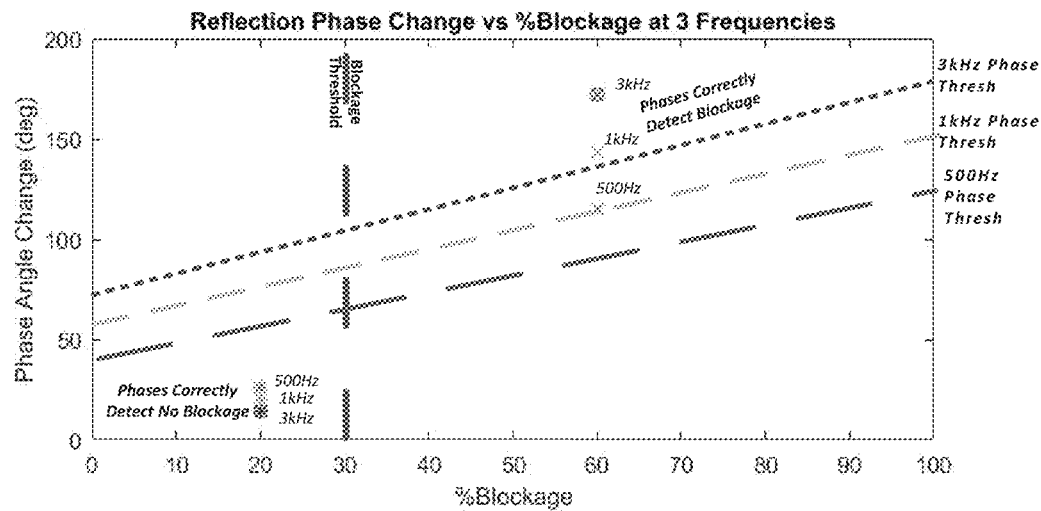
Fig. 9G

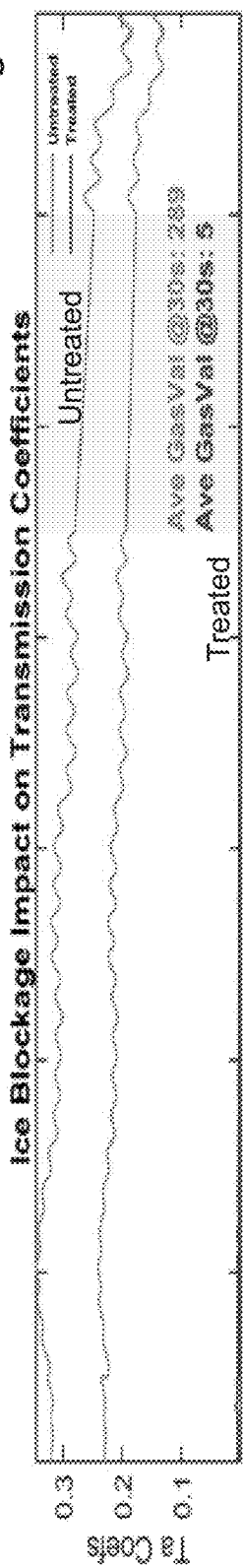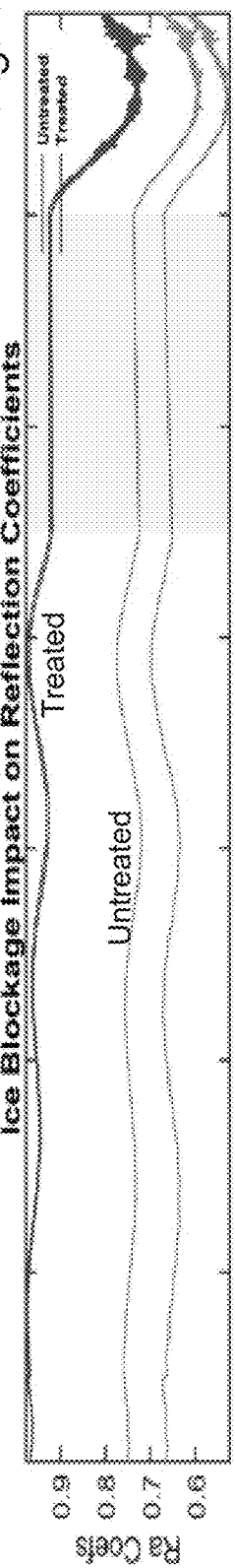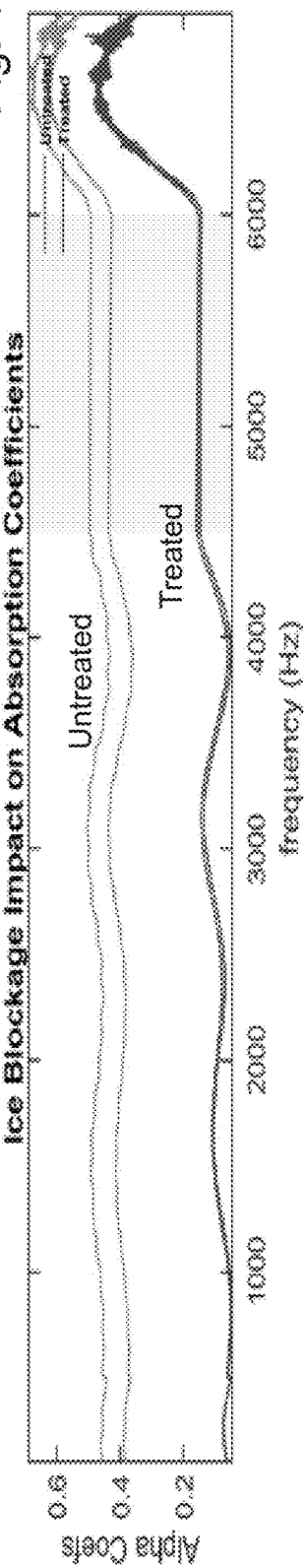

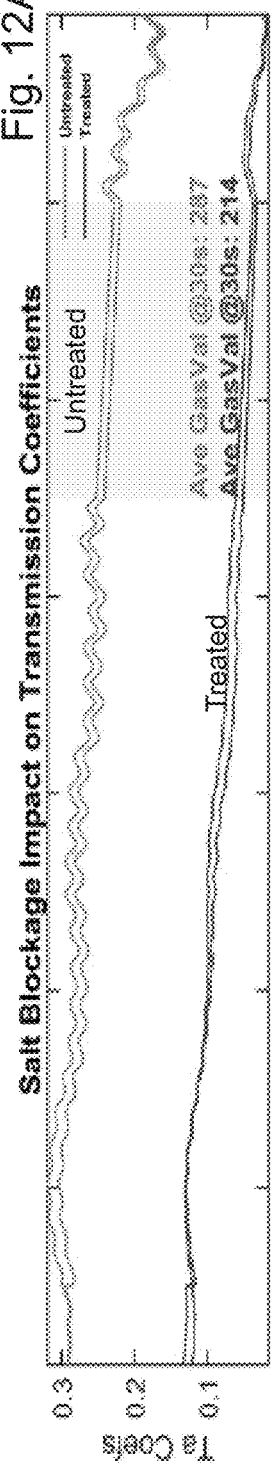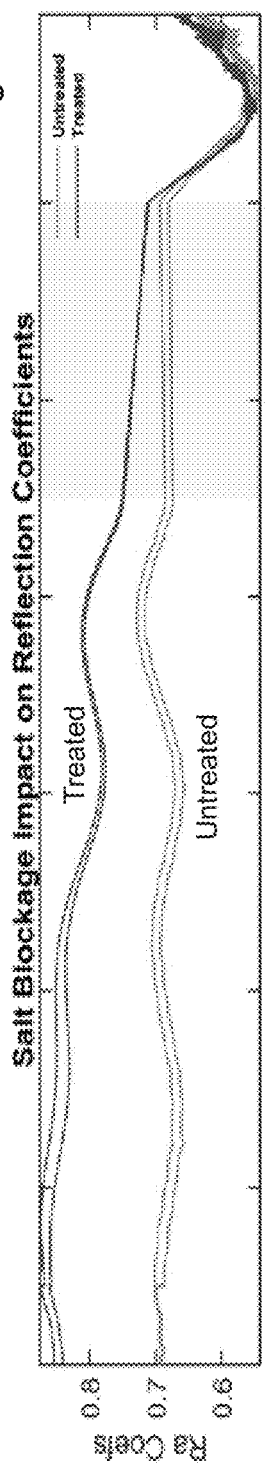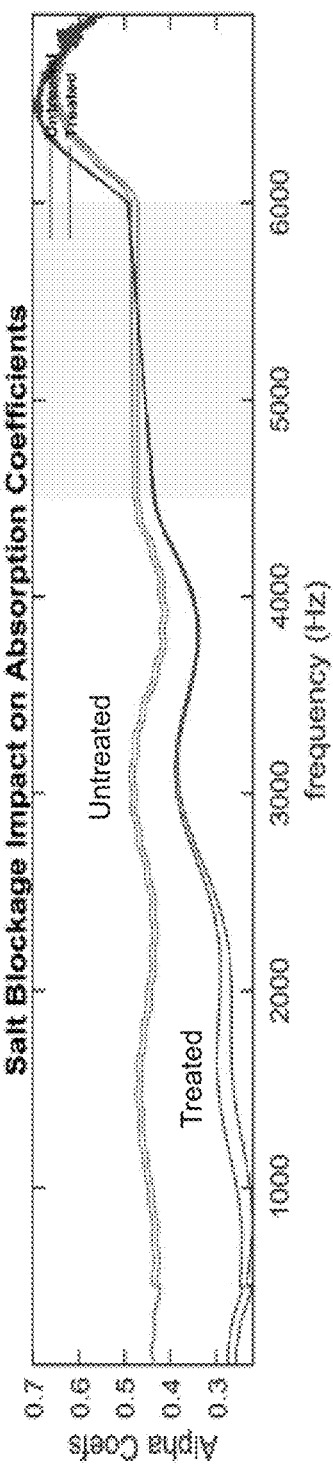

DETECTION OF BLOCKAGE IN A POROUS MEMBER

CROSS-REFERENCE TO RELATED APPLICATIONS

This application claims benefit of U.S. Provisional Patent Application Ser. No. 62/291,823, filed Feb. 5, 2016, the disclosure of which is incorporated herein by reference.

BACKGROUND

The following information is provided to assist the reader in understanding technologies disclosed below and the environment in which such technologies may typically be used. The terms used herein are not intended to be limited to any particular narrow interpretation unless clearly stated otherwise in this document. References set forth herein may facilitate understanding of the technologies or the background thereof. The disclosure of all references cited herein are incorporated by reference.

Many gas sensors include gas porous members/barriers or diffusion barriers that separate or partition the analytical components of the sensor from the environment the sensor is intended to monitor. Such porous members are commonly used to reduce or eliminate ingress of contaminants that may impede the operation of the sensor's analytical components and/or to isolate the analytical components as a source of ignition in the environment to which the sensor is exposed. When such porous members are used, the analyte gas(es) to be detected/monitored by the sensor must pass through the porous member to reach the analytical components of the sensor. The capability and effectiveness of analyte transport through the porous member directly impacts the speed, precision and accuracy with which the sensor can respond to changes in the relative concentration of the analyte in the external, ambient environment being monitored. As a consequence, porous members are designed and/or selected such that the analyte transport through the porous member, in concert with the analytical components of the sensor, enable the sensor to respond to levels and/or changes in the relative levels of the analyte in the monitored environment at the nominal or minimal rate, precision and accuracy defined by the sensing application. Once a sensor is deployed, extraneous contaminants (arising in the normal operating environment or resulting from atypical events or maintenance activities) contacting or penetrating the porous member can either directly, or as a consequence of reaction with the porous member, inhibit analyte transport between the environment and the analytical components of the sensor. Such an inhibition in analyte transport through the porous member, resulting in deviation from the target sensor response rate to the analyte and/or deviation in precision/accuracy in assessment of absolute or relative changes in analyte concentration, is designated by the term "blockage" or "blocking". Additionally, the contaminant or condition causing the blocking is commonly referred to as the "blockage". A common example of blockage occurs in industrial environments where sensor response to the analyte can become partially or completely inhibited by overpainting, water, dirt/mud, insect or animal deposits, or by other extraneous diffusion-impeding substances. Failure to identify impairment of transport through the sensor porous member can result in under-detection or non-detection of analyte concentration levels exceeding safe environmental limits.

In addition to blockage of a diffusion or other sensor porous member, performance of the sensor itself may degrade over time. Prudence thus dictates that gas detection instrumentation be tested regularly for functionality. It is a common practice to, for example, perform a "bump check," or functionality check on portable gas detection instrumentation on a daily basis. The purpose of this test is to ensure the functionality of the entire gas detection system, commonly referred to as an instrument. A periodic bump check or functionality check may also be performed on a permanent gas detection instrument to, for example, extend the period between full calibrations. Gas detection systems include at least one gas sensor, electronic circuitry and a power supply to drive the sensor, interpret its response and display its response to the user. The systems further include a housing to enclose and protect such components. A bump check typically includes: a) applying a gas of interest (usually the target gas or the analyte gas which the instrument is intended to detect); b) collecting and interpreting the sensor response; and c) indicating to the end user the functional state of the system (that is, whether or not the instrument is properly functioning).

As described above, such bump tests are performed regularly and, typically, daily for portable gas detection instruments. Bump checks provide a relatively high degree of assurance to the user that the gas detection device is working properly. The bump check exercises all the necessary functionalities of all parts of the gas detection device in the same manner necessary to detect an alarm level of a hazardous gas. In that regard, the bump check ensures that there is efficient gas delivery from the outside of the instrument, through any transport paths (including, for example, any protection and/or diffusion member or membranes) to contact the active sensor components. The bump check also ensures that the detection aspect of the sensor itself is working properly and that the sensor provides the proper response function or signal. The bump check further ensures that the sensor is properly connected to its associated power supply and electronic circuitry and that the sensor signal is interpreted properly. Moreover, the bump check ensures that the indicator(s) or user interface(s) (for example, a display and/or an annunciation functionality) of the gas detection instrument is/are functioning as intended.

However, a periodic/daily bump check requirement has a number of significant drawbacks. For example, such bump checks are time consuming, especially in facilities that include many gas detection systems or instruments. The bump check also requires the use of expensive and potentially hazardous calibration gases (that is, the analyte gas or a simulant therefor to which the sensor is responsive). Further, the bump check also requires a specialized gas delivery system, usually including a pressurized gas bottle, a pressure reducing regulator, and tubing and adapters to correctly supply the calibration gas to the instrument. The requirement of a specialized gas delivery system often means that the opportunity to bump check a personal gas detection device is limited in place and time by the availability of the gas delivery equipment.

Recently, a number of systems and methods have been proposed to reduce the number of bump tests required. Such systems may, for example, include electronic interrogation of a sensor and/or a test of the transport path to the sensor, including through a diffusion or other barrier (without application of an analyte gas or a simulant therefor). Nonetheless, it remains desirable to develop improved testing systems and methodologies for reducing the number of bump checks required for sensors.

SUMMARY

In one aspect, a method of detecting at least a partial blockage in a porous member separating an inner chamber of a device having a gas sensor responsive to an analyte positioned within the inner chamber and an ambient environment includes emitting pressure waves within the inner chamber and measuring a response via a sensor responsive to pressure waves positioned within the inner chamber. Emitting pressure waves within the inner chamber may, for example, include activating a speaker positioned within the inner chamber (to, for example, emit acoustic waves). Measuring the response via the sensor responsive to pressure waves may, for example, include measuring the response via a microphone positioned within the inner chamber. In a number of embodiments, pressure waves are emitted at a plurality of frequencies within the chamber and a response is measured at more than one of the plurality of frequencies.

Measuring a response may, for example, include measuring at least one of transmission, reflection or absorbance (of the pressure waves). At least one of a change in amplitude and a change in phase may, for example, be measured. In a number of embodiments, a change in phase is measured. In a number of embodiments, each of a change in amplitude and a change in phase is measured. A lock-in algorithm may, for example, be used to measure each of the change in amplitude and the change in phase. Phase and amplitude may, for example, be measured at each of a plurality of frequencies of the emitted pressure waves.

At least one of the plurality of frequencies of the emitted pressure waves may, for example, be a self-resonant frequency of the porous member, and a response measured at that frequency may be associable with a blockage that infiltrates pores of the porous membrane. A measured response may, for example, be used to discriminate between at least a partial blockage associated with an outside surface of the porous member and at least a partial blockage infiltrating pores of the porous member.

In another aspect, a gas sensor device to detect an analyte gas in an ambient environment includes a housing including an inner chamber and a port, a porous member in operative connection with the port to separate the inner chamber from the ambient environment, a sensor responsive to the analyte positioned within the inner chamber, a source of pressure waves positioned within the inner chamber, a sensor responsive to pressure waves positioned within the inner chamber; and circuitry in operative connection with the sensor responsive to pressure waves to relate a response of the sensor responsive to pressure waves to blockage in the porous member. The source of pressure waves may, for example, include a speaker, and the sensor responsive to pressure waves may, for example, include a microphone. The speaker may, for example, emit acoustic waves or sound. Acoustic waves may be emitted at a plurality of frequencies.

The circuitry may, for example, measure at least one of transmission, reflection or absorbance of the pressure waves. In a number of embodiments, the circuitry measures at least one of a change in amplitude and a change in phase. The circuitry may, for example, measure a change in phase. In a number of embodiments, the circuitry measures each of a change in amplitude and a change in phase. Each of a change in phase and a change in amplitude may be measured at more than one of the plurality of frequencies of the emitted pressure waves.

The circuitry may, for example, include a processor system in operative connection with a memory system. The memory system may, for example, include a lock-in algorithm executable by the processing system to measure each of the change in amplitude and the change in phase.

At least one of a plurality of frequencies of emitted pressure waves may, for example, be a self-resonant frequency of the porous member, and a response measured at the at least one of the plurality of frequencies may be associable with a blockage that infiltrates pores of the porous membrane. The circuitry may, for example, be adapted to use the measured response to discriminate between at least a partial blockage associated with an outside surface of the porous member and at least a partial blockage infiltrating pores of the porous member.

In another aspect, a method of detecting at least a partial blockage in a porous member separating an inner chamber of a device having a gas sensor responsive to an analyte positioned within the inner chamber and an ambient environment includes emitting pressure waves within the inner chamber and measuring a change in phase of a response via a sensor responsive to pressure waves. The change in phase of the response may, for example, be measured via the sensor responsive to pressure waves which is positioned within or located within the inner chamber. The method may further include measuring a change in magnitude of the response. In a number of embodiments, the change in phase of the response is measured at more than one frequency. In a number of embodiments, the change in phase and the change in magnitude of the response are measured at more than one frequency.

Measuring the response may, for example, include measuring at least one of transmission, reflection or absorbance. In a number of embodiments, a lock-in algorithm is used to measure each of the change in amplitude and the change in phase. At least one of the more than one frequency may, for example, be a self-resonant frequency of the porous member and a response measured at the at least one of the more than one frequency may be associable with a blockage that infiltrates pores of the porous membrane.

The method may further include using the measured response to discriminate between at least a partial blockage associated with an outside surface of the porous member and at least a partial blockage infiltrating pores of the porous member. Pressure waves may, for example, be emitted at a self-resonant frequency of the porous member and a response measured at the self-resonant frequency may be associated with a determination of the at least a partial blockage infiltrating pores of the porous membrane.

In another aspect, a gas sensor device to detect an analyte gas in an ambient environment includes a housing including an inner chamber and a port, a porous member in operative connection with the port to separate the inner chamber from the ambient environment, a sensor responsive to the analyte gas positioned within the inner chamber, a source of pressure waves positioned within the inner chamber, a sensor responsive to pressure waves, and circuitry in operative connection with the sensor responsive to pressure waves to relate a phase response of the sensor responsive to pressure waves to blockage in the porous member. The sensor responsive to pressure waves may be positioned within the inner chamber. The circuitry may also be adapted to further effect other actions and/or functions as described herein.

In another aspect, a method of detecting at least a partial blockage in a porous member separating an inner chamber of a device having a gas sensor responsive to an analyte positioned within the inner chamber and an ambient environment includes emitting pressure waves within the inner chamber and measuring a change in a response at more than one frequency via a sensor responsive to pressure waves.

The change in the response may, for example, be measured via the sensor responsive to pressure waves which is located within or positioned within the inner chamber. A change in phase of the response may be measured at each frequency. In a number of embodiments, a change in magnitude of the response is measured at each frequency. In a number of embodiments, a change in phase and a change in magnitude of the response are measured at each frequency.

Measuring the response comprises measuring at least one of transmission, reflection or absorbance. In a number of embodiments, a lock-in algorithm is used to measure each of the change in amplitude and the change in phase. At least one of the more than one frequency may, for example, be a self-resonant frequency of the porous member and a response measured at the at least one of the more than one frequency may be associable with a blockage that infiltrates pores of the porous membrane.

In another aspect, a gas sensor device to detect an analyte gas in an ambient environment includes a housing including an inner chamber and a port, a porous member in operative connection with the port to separate the inner chamber from the ambient environment, a sensor responsive to the analyte positioned within the inner chamber, a source of pressure waves positioned within the inner chamber adapted to emit pressure waves at more than one frequency, a sensor responsive to pressure waves and circuitry in operative connection with the sensor responsive to pressure waves to relate a response of the sensor responsive to pressure waves at each of the more than one frequency to blockage in the porous member. The sensor responsive to pressure waves may be positioned within the inner chamber. The circuitry may also be adapted to further effect other actions and/or functions as described herein.

In another aspect, a method of detecting at least a partial blockage in a porous member separating an inner volume of a device and a volume outside the device includes emitting pressure waves within the inner chamber and measuring a change in phase of a response via a sensor responsive to pressure waves. In general, the methods and devices described herein may be used to detect at least a partial blockage in any device or system including a porous member.

In another aspect, a device includes a housing having an inner chamber and a port, a porous member in operative connection with the port to separate the inner chamber from the ambient environment, a source of pressure waves positioned within the inner chamber, a sensor responsive to pressure waves, and circuitry in operative connection with the sensor responsive to pressure waves to relate a phase response of the sensor responsive to pressure waves to blockage in the porous member. The sensor responsive to pressure waves may be positioned within the inner chamber. The circuitry may also be adapted to further effect other actions and/or functions as described herein.

In a further aspect, a method of detecting at least a partial blockage in a porous member separating an inner volume of a device and a volume outside the device includes emitting pressure waves within the inner chamber and measuring a change in response at more than one frequency via a sensor responsive to pressure waves positioned within the inner chamber. In a number of embodiments, a change in phase of the response is measured at each frequency. In a number of embodiments, a change in magnitude of the response is measured at each frequency. In a number of embodiments, a change in phase and a change in magnitude of the response are measured at each frequency.

In still a further aspect, a device, includes a housing having an inner chamber and a port, a porous member in operative connection with the port to separate the inner chamber from the ambient environment, a source of pressure waves positioned within the inner chamber adapted to emit pressure waves at more than one frequency, a sensor responsive to pressure waves, and circuitry in operative connection with the sensor responsive to pressure waves to relate a response of the sensor responsive to pressure waves at each of the more than one frequency to blockage in the porous member. The sensor responsive to pressure waves may be positioned within the inner chamber. The circuitry may also be adapted to further effect other actions and/or functions as described herein.

The present devices, systems, and methods, along with the attributes and attendant advantages thereof, will best be appreciated and understood in view of the following detailed description taken in conjunction with the accompanying drawings.

BRIEF DESCRIPTION OF THE DRAWINGS

FIG. 8 illustrates reflection coefficient phase change over a range of blockage percent for the porous metal frit of the gas sensor device of FIG. 4.

FIG. 9F illustrates a representative blockage classification using magnitude response at multiple interrogation frequencies demonstrated for the case of 20% and 60% blockage with frequency dependent thresholding.

FIG. 9G illustrates a representative blockage classification using phase response at multiple interrogation frequencies demonstrated for the case of 20% and 60% blockage with frequency dependent thresholding.

FIG. 11A illustrates transmission coefficient change in the case of ice blockage of the porous metal frit of the gas sensor device of FIG. 4 over a range of frequencies.

FIG. 11B illustrates reflection coefficient change in the case of ice blockage of the porous metal frit of the gas sensor device of FIG. 4 over a range of frequencies.

FIG. 11C illustrates absorption coefficient change in the case of ice blockage of the porous metal frit of the gas sensor device of FIG. 4 over a range of frequencies.

FIG. 12A illustrates transmission coefficient change in the case of salt blockage of the porous metal frit of the gas sensor device of FIG. 4 over a range of frequencies.

FIG. 12B illustrates reflection coefficient change in the case of salt blockage of the porous metal frit of the gas sensor device of FIG. 4 over a range of frequencies.

FIG. 12C illustrates absorption coefficient change in the case of salt blockage of the porous metal frit of the gas sensor device of FIG. 4 over a range of frequencies.

DETAILED DESCRIPTION

Figure 1:
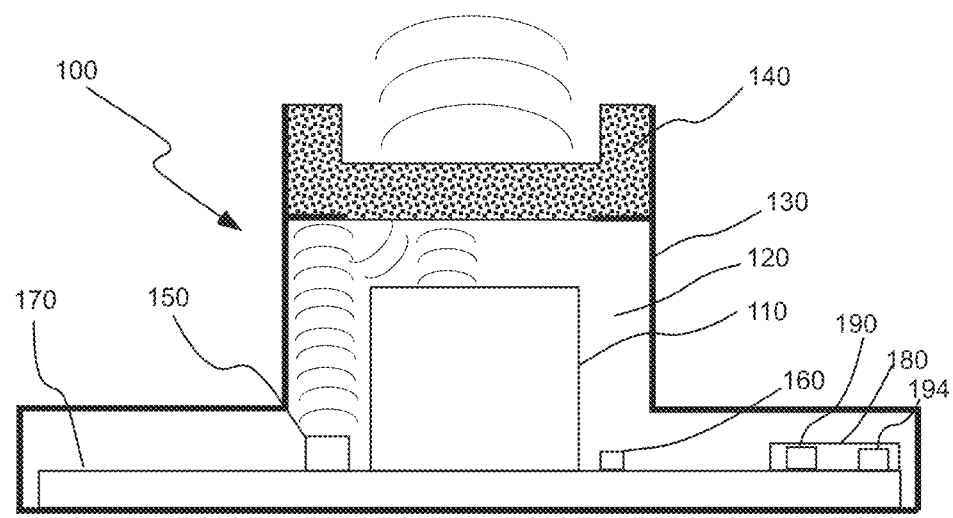
FIG. 1 illustrates an embodiment of a gas sensor device hereof.

It will be readily understood that the components of the embodiments, as generally described and illustrated in the figures herein, may be arranged and designed in a wide variety of different configurations in addition to the described representative embodiments. Thus, the following more detailed description of the representative embodiments, as illustrated in the figures, is not intended to limit the scope of the embodiments, as claimed, but is merely illustrative of representative embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, described features, structures, or characteristics may be combined in any suitable manner in one or more embodiments. In the following description, numerous specific details are provided to give a thorough understanding of various embodiments. One skilled in the relevant art will recognize, however, that the various embodiments can be practiced without one or more of the specific details, or with other methods, components, materials, et cetera. In other instances, well known structures, materials, or operations are not shown or described in detail to avoid obfuscation.

As used herein and in the appended claims, the singular forms "a," "an", and "the" include plural references unless the context clearly dictates otherwise. Thus, for example, reference to "a sensor" includes a plurality of such sensors and equivalents thereof known to those skilled in the art, and so forth, and reference to "the sensor" is a reference to one or more such sensors and equivalents thereof known to those skilled in the art, and so forth. Recitation of ranges of values herein are merely intended to serve as a shorthand method of referring individually to each separate value falling within the range. Unless otherwise indicated herein, and each separate value, as well as intermediate ranges, are incorporated into the specification as if individually recited herein. All methods described herein can be performed in any suitable order unless otherwise indicated herein or otherwise clearly contraindicated by the text.

As used herein, the term "circuit" or "circuitry" includes, but is not limited to, hardware, firmware, software or combinations of each to perform a function(s) or an action(s). For example, based on a desired feature or need, a circuit may include a software controlled microprocessor, discrete logic such as an application specific integrated circuit (ASIC), or other programmed logic device. A circuit may also be fully embodied as software.

The term "control system" or "controller," as used herein includes, but is not limited to, any circuit or device that coordinates and controls the operation of one or more input or output devices. For example, a controller can include a device having one or more processors, microprocessors, or central processing units (CPUs) capable of being programmed to perform input or output functions.

The term "processor," as used herein includes, but is not limited to, one or more processor systems or stand-alone processors, such as microprocessors, microcontrollers, central processing units (CPUs), and digital signal processors (DSPs), in any combination. A processor may be associated with various other circuits that support operation of the processor, such as a memory system (for example, random access memory (RAM), read-only memory (ROM), programmable read-only memory (PROM), erasable programmable read only memory (EPROM)), clocks, decoders, memory controllers, or interrupt controllers, etc. These support circuits may be internal or external to the processor or its associated electronic packaging. The support circuits are in operative communication with the processor. The support circuits are not necessarily shown separate from the processor in block diagrams or other drawings.

As a metric, blockage may directly designate impedance of analyte transport through the porous member and/or designate the consequential changes in sensor performance resulting from this transport impedance. Blockage may, for example, be metered in a continuous measure. For example, blockage may be metered as a percentage, ranging from 0% when analyte transport through the porous member is normal or nominal to 100% marking total inhibition of analyte transport between the sensor analytical components and the monitored environment. Blockage may also be metered as discrete states with designations such as unblocked (indicating typical or normal analyte transport through the porous member) or partial (indicating impedance of analyte transport beyond typical or normal but less than complete transport inhibition) or complete (indicating total inhibition of analyte transport through the porous member). Alternatively, blockage can be ascribed to boolean states, with an unblocked state indicating inhibition of analyte transport through the porous member falls below a designated acceptable limit, and a blocked state indicating analyte transport inhibition exceeds the designated limit. Adequate measure in detecting and designating blockage (and/or resultant impairment to sensor performance) is important for assurance of sensor function. As describe above, failure to identify impairment of transport through the sensor porous member can result in under-detection or non-detection of analyte concentration levels exceeding safe environmental limits.

In a number of embodiments, devices, systems and methods hereof are used to detect flow through a porous member, membrane or barrier (for example, a diffusion barrier) of, for example, a sensor for detecting a target or an analyte gas. Such porous members may, for example, be porous metal frits or porous polymeric membranes in a number of representative embodiments. In a number of embodiments, a source, generator or transmitter of pressure waves or acoustic waves such as a speaker is played into a volume or chamber behind (that is, on the sensor side and opposite the ambient side) of a porous member such as a porous frit or a porous membrane. A response to the generated acoustic/pressure waves (for example, sound) is measured by a pressure wave sensor, acoustic sensor or receiver such as a microphone and is related to gas transport through the membrane. In general, any sensor or receiver that is responsive to pressure changes or waves of pressure propagated in a medium (for example, air) may be used herein. Such sensors or receivers are sometimes referred to herein generally as acoustic sensors or receivers.

The present devices, systems and methods may, for example, be used in fixed or portable gas instruments, but are particularly beneficial in fixed gas instruments. In the case of a fixed (as opposed to portable) gas instrument, the instrument is calibrated when it is put into service. As described above, after placement in service, it is recommended to frequently "bump test" the instrument to check for gas flow to the sensor and that the sensor responds as expected. As also described above, to bump test an instrument, the user applies a target/analyte gas (or a simulant gas to which the sensor is responsive) of a known concentration to the instrument and checks the instrument for an expected or acceptable response. If the sensor response is acceptable (using, for example, predetermined thresholds), the user can then calibrate the instrument to the known concentration of the target gas.

Using electronic interrogation systems and methods as described, for example, in U.S. Pat. Nos. 7,413,645, 7,959,777 and U.S. Patent Application Publication Nos. 2014/0273263, 2013/0193004, 2013/0192332, 2013/0186776, 2013/0186777, and U.S. patent application Ser. No. 15/012,919, the disclosures of which are incorporated herein by reference, one has the ability to electronically interrogate a sensor, determine changes in sensor performance thereby, and compensate sensor output so that the sensor response is acceptable, thereby extending the period of time between (or eliminating) bump checks. Electronic interrogation of a sensor may, for example, include applying electrical energy to an electrode or sensor element and measuring a response to the application of electrical energy and/or an electrical property of the electrode or sensor element to determine a state of the sensor. Electronically interrogating a sensor, however, cannot account for or detect blockage of the porous member that separates/protects the sensor from the ambient environment or outside world. Combining electronic interrogation of the sensor with systems, devices and methods of detecting blockage of such a porous member, provides the ability to further reduce or eliminate bump testing the instrument.

In a number of representative embodiments hereof, to detect a blockage of a porous member separating a gas sensor from the ambient environment (in which the concentration of the analyte gas it to be determined) an acoustic wave or waves transmitted from a source/speaker interacts with the porous member and with any blockage thereof. Signals are then received by an acoustic sensor/microphone. The response is processed and correlated to a loss in flow through the porous member and/or, in the case of a sensor, a loss in gas response of the sensor. There are a number of ways to analyze and/or to process the data to determine the presence and/or degree of a blockage. In a number of embodiments, the source/speaker and the acoustic sensor are positioned or located on the same side of the porous member as the gas sensor.

In a number of studied embodiments hereof, a combustible gas sensor device 100 was tested which included a sensor 110 within an inner chamber 120 created by an explosion-proof housing 130 and a porous member in the form of a porous frit 140. Catalytic combustible gas sensor devices and electronic interrogation thereof are, for example, described in U.S. Patent Application Publication No. 2014/0273263, the disclosure of which is incorporated herein by reference. Although combustible gas sensors were studied in a number of representative embodiments hereof, the devices, systems and method hereof can be used in connection with any sensor (for example, electrochemical sensors, photoacoustic sensors, etc.) or other device in which a porous member or membrane separates an inner chamber or volume from an outside environment. In the embodiment of device 10, a speaker 150 and a microphone 160 are also positioned within chamber 120. It is not necessary to acoustically isolate speaker 150 and microphone 160 from the remainder of inner chamber 120 and sensor 110 or to narrowly channel the propagation of acoustic/pressure waves therebetween. In the illustrated embodiment, sensor 110, speaker 150 and microphone 160 are in electrical connection with circuitry including a printed circuit board 170 which may be in electrical connection with control circuitry 180 illustrated schematically in FIG. 1, which may be positioned within and/or outside of explosion proof housing 130. Control circuitry 180 may for example, include a processor system 190 (including one or more processors such as microprocessors) and a memory system 194 in operative connection with processor system 190. Memory system 194 may, for example, include one or more algorithms stored therein and executable by processor system 190.

As illustrated, for example, in FIG. 1, acoustic waves propagate within chamber 120 toward frit 140. Without limitation to any mechanism, some of the acoustic waves pass into frit 140, and some of the sound waves are reflected back into inner chamber 120. In that regard, of the acoustic waves that pass into frit 140, some are absorbed in frit 140, some are reflected back into inner chamber 130 (from which the acoustic waves emanated), and some pass through frit 140 into the ambient environment outside of explosion proof housing 130. The acoustic waves that are passed through frit 140 and outside of explosion-proof housing 130 are "lost" acoustic waves, which are very relevant to the degree of blockage of frit 140. When frit 140 is blocked, less acoustic waves (for example, sound waves) are lost, and more acoustic waves are reflected back into chamber 120. In a number of studies, multiple frequencies were generated by speaker 150. If, for example, one looks at what sound is received by microphone 160 in the frequency domain, one should be able to readily pick out the frequencies that were generated. Once can then set a threshold at each frequency for a magnitude and/or phase for what a blocked or unblocked response should be. Analysis may also be made in the time domain (wherein thresholds may, for example, be set for a magnitude and/or time delay of a response). In the time domain, a driving force including multiple frequencies may, for example, be generated by the speaker.

In experiments with generating various frequencies and measuring the response on microphone 160, it was unexpectedly discovered that at some frequencies the response was actually quieter/decreased when frit 140 was blocked. It was also found that the resonances of chamber 120 may be significant, and in the same frequency region as the interrogation signal.

Figure 2:
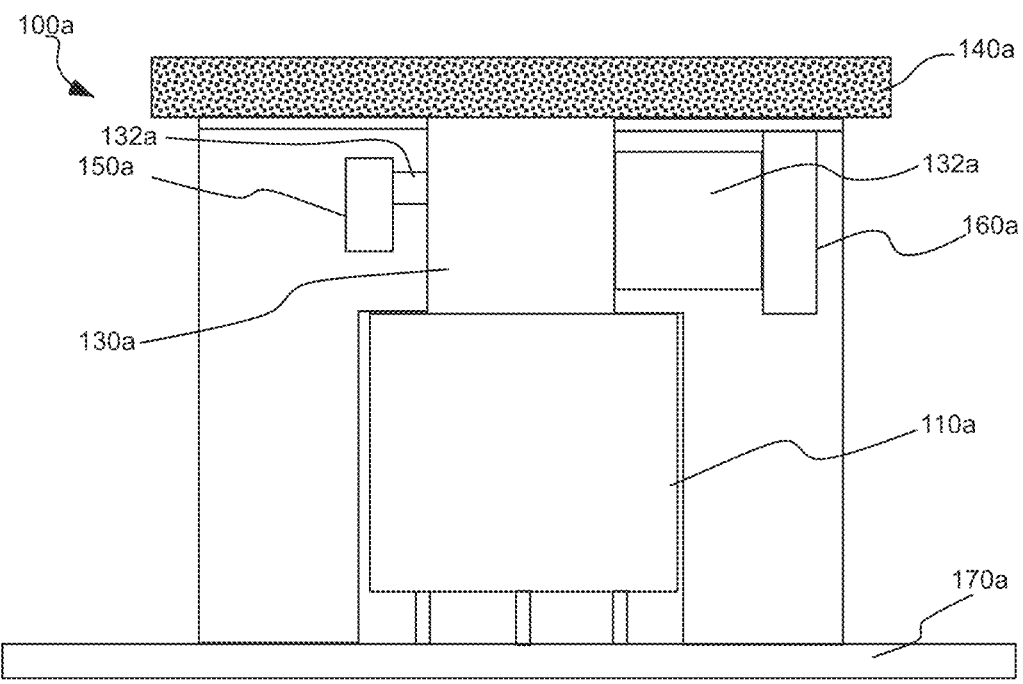
FIG. 2 illustrates another embodiment of a gas sensor device hereof
Figure 3:
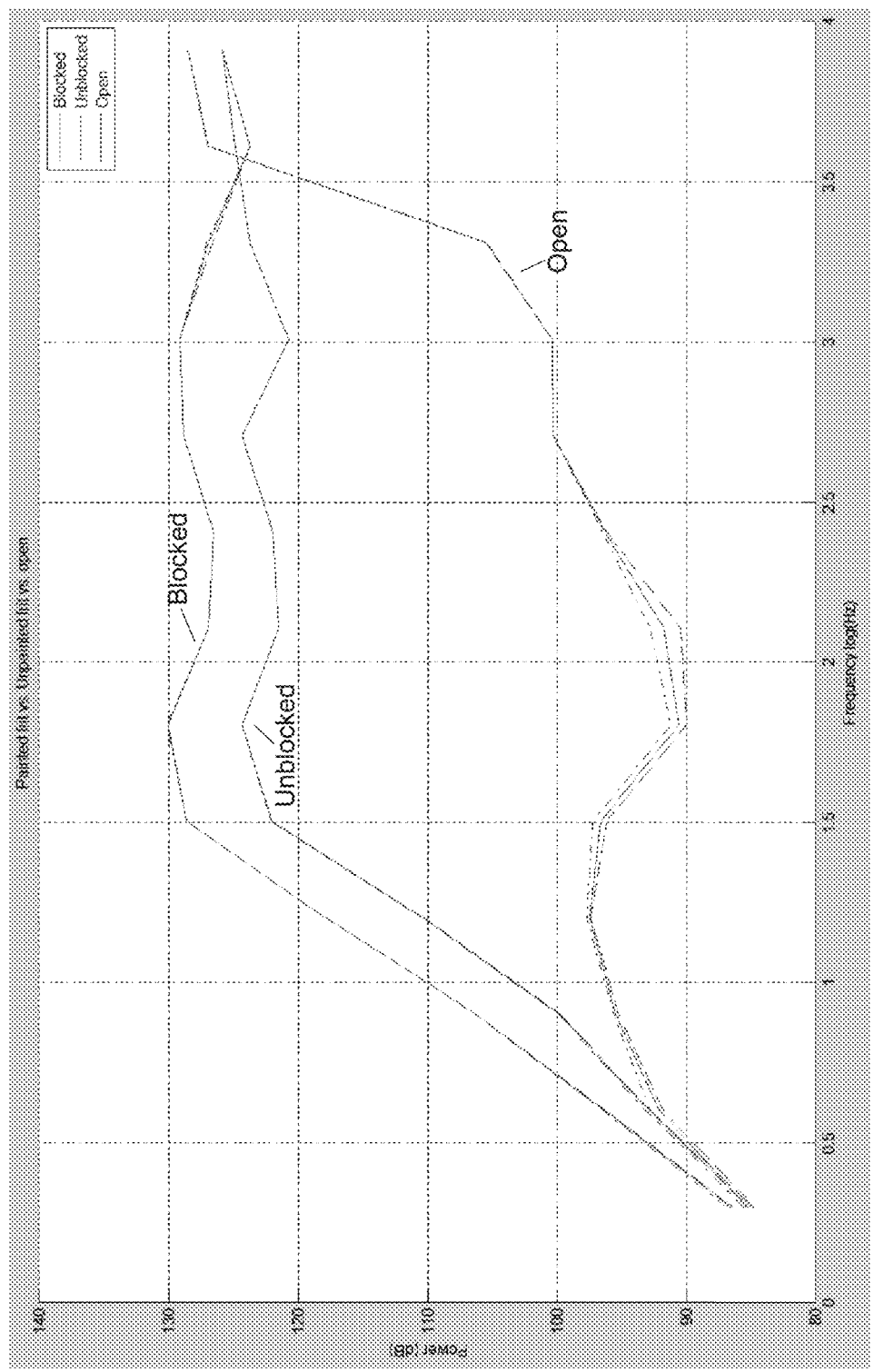
FIG. 3 illustrates pressure or audio sensor response over a range of frequencies for a blocked and unblocked porous metal frit in the sensor of FIG. 2.

To address resonances within the inner chamber, a combustible gas sensor device 100a, illustrated without a housing in FIG. 2, was manufactured wherein a speaker 150a and microphone 160a were positioned within a channel or channels 132a in acoustic connection with chamber 130a between frit 140a and sensor 110a. It was found that sound pressure level (SPL) received by microphone 160a and also the SPL directed at frit 140a were increased as compared to combustible gas sensor device 100. Because the SPL was increased, the signal response was increased between a blocked and an unblocked state. FIG. 3 shows data from a representative response vs. frequency study for a blocked frit, an unblocked frit, and an open frit (that is, the absence of a frit).

Combustible gas sensor device 100a did not exhibit the resonances experienced with combustible gas sensor device 100 and, as indicated above, exhibited a greater difference in the response from a blocked to an unblocked state. A disadvantage of the design of combustible gas sensor device 100b, however, is difficulty of manufacture.

Figure 4:
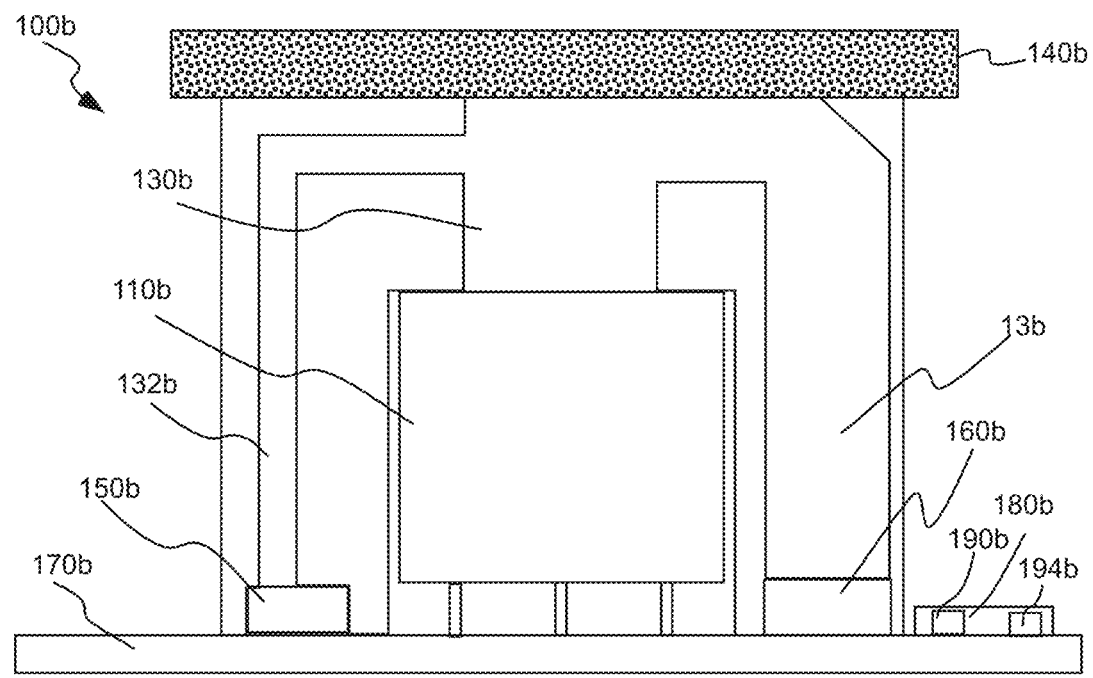
FIG. 4 illustrates another embodiment of a gas sensor device hereof.
Figure 5:
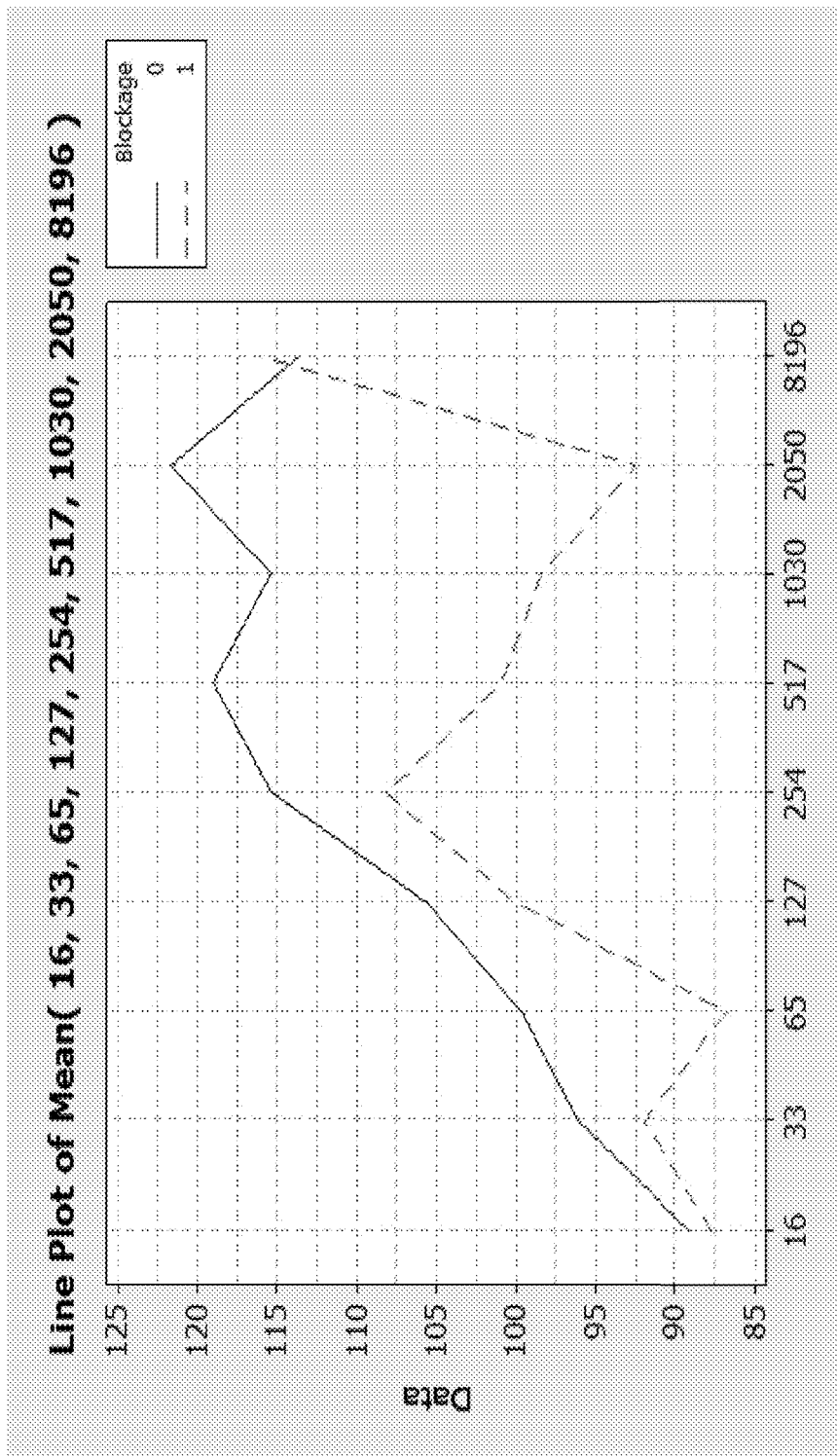
FIG. 5 illustrates pressure or acoustic sensor response over a range of frequencies for a blocked and unblocked porous metal frit in the sensor of FIG. 4.

In device 100b of FIG. 4, speaker 150b and microphone 160b were positioned adjacent or on printed circuit board 170b. A control system including a microprocessor 190b and memory 194b was also incorporated on printed circuit board 170b to control the system and execute computations required to detect blockage. Unlike device 100, however, speaker 150b and microphone 160b were ported directly to a volume of chamber 130b between sensor 110b and frit 140b via channels 132b and 134b, respectively. The design of device 100b of FIG. 4 decreased the volume of chamber 130b within which sensor 110b, microphone 150b, and speaker 160b were positioned (as compared to device 100 of FIG. 1), while significantly improving manufacturability as compared to device 100a of FIG. 2. The smaller chamber of device 100b provided a number of advantages over the case in which porting was not used. In that regard, sensor response was faster because less air had to be exchanged with the ambient air that was being monitored. Furthermore, the volume (loudness) of the signal from speaker 150b that was received by microphone 160 was increased because speaker 150b had to drive a smaller volume chamber. FIG. 5 illustrates the difference in reflectance coefficient amplitude response between a frit 140b blocked with paint and an unblocked frit 140b over a range of frequencies, with frequency on the x-axis and the magnitude of the measured response on the y-axis.

Figure 6:
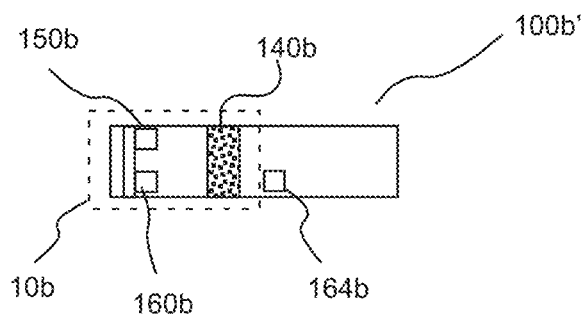
FIG. 6 illustrates an embodiment of a test system used to study gas sensor devices as illustrated in FIG. 4.

Based on the design of device 100b of FIG. 4, a test system 100b' (illustrated schematically in FIG. 6) was constructed in which different frits 140b, with and without various types of blockage, could be readily placed in operative connection with test system 100b' and removed from connection therewith. Test system 100b' further includes a second acoustic sensor/microphone 164b positioned outside of frit 140b. The measured output from test system 100b' included changes in the phase and magnitude response of the transmission coefficient (measured by microphone 164b), reflection coefficient (measured by microphone 160b) and absorption coefficient (calculated). Systems hereof may measure reflected energy and/or transmitted energy. Measuring reflected energy alone provides the benefit of use of an acoustic sensor or microphone only within the enclosure of a device. Further, in the case of, for example, a sensor used in environments where hazardous, combustible and/or explosive gases may be present, enclosure of the acoustic sensor within an explosion proof housing eliminates a potential ignition source. However, intrinsically safe circuitry and/or additional protection may be used for an acoustic sensor or microphone placed outside of a porous member in environments in which hazardous, combustible and/or explosive gases may be present.

Figure 7:
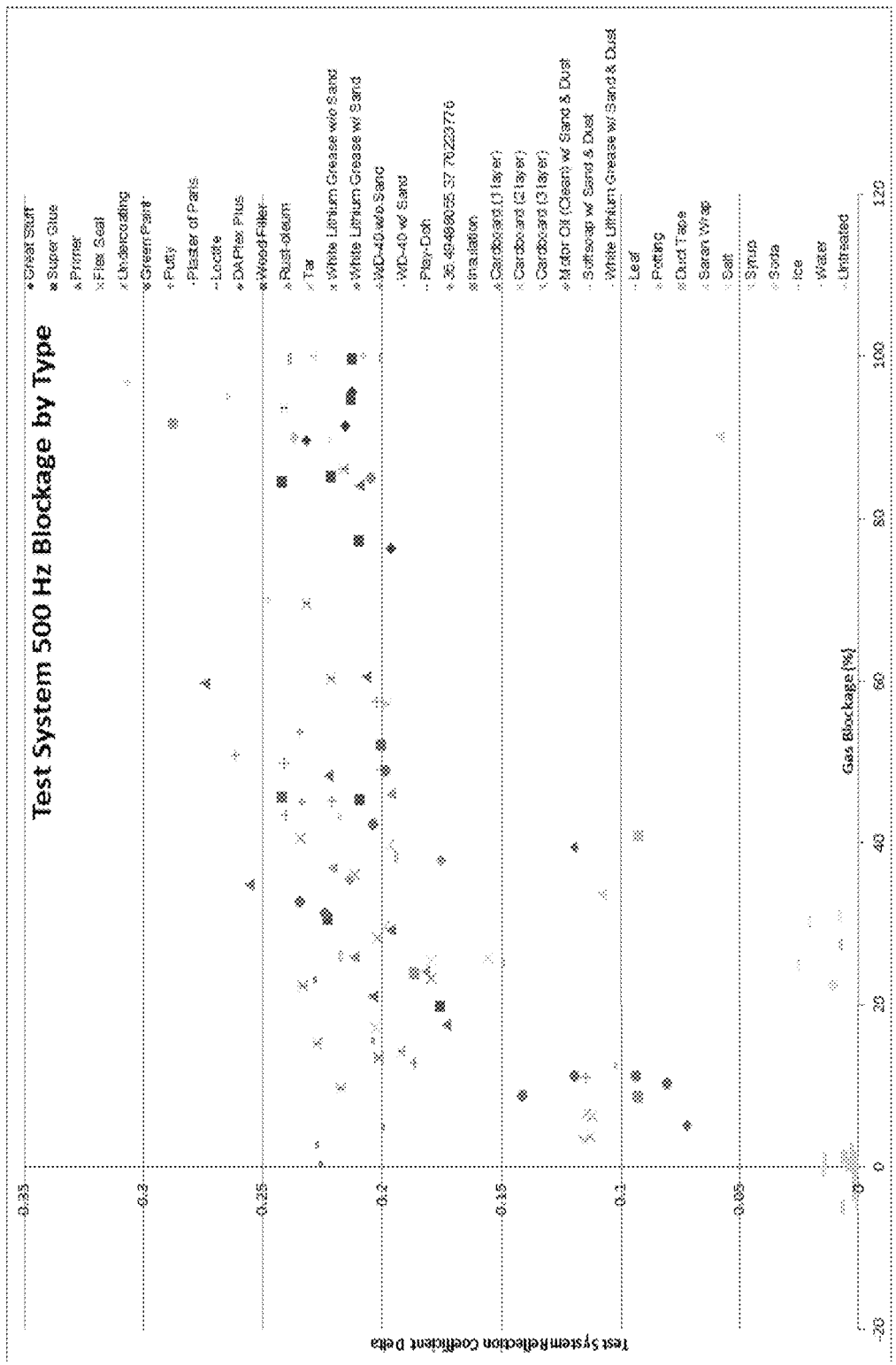
FIG. 7 illustrates reflection coefficient amplitude change over a range of blockage percent for the porous metal frit of the gas sensor device of FIG. 4.

In a number of studies, reflectance and/or transmission were measured at one or more frequencies for each tested frit 140b. FIGS. 7 and 8, respectively, illustrate representative magnitude and phase response for various blockage types at a frequency of 500 Hz. Although information regarding blockage of frit 140b can be obtained from changes in either phase or magnitude of, for example, measured reflectance and/or transmission data. It has been discovered that it may be beneficial to analyze each of phase and magnitude. In that regard, at a particular frequency, a certain type of blockage may cause a significant change in magnitude and very little or no change in phase. Similarly, at a particular frequency, a certain type of blockage may cause a significant change in phase and very little or no change in magnitude.

Figure 9A:
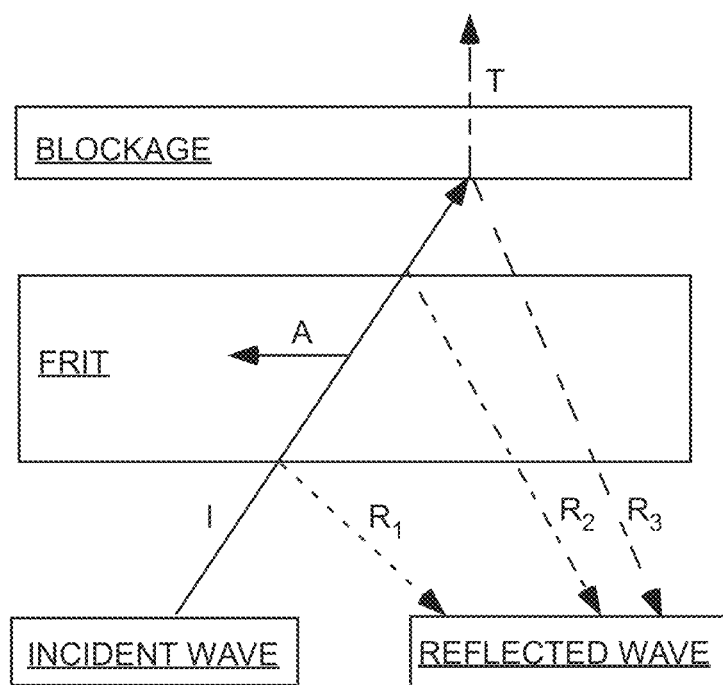
FIG. 9A illustrates schematically the transmission (T), reflectance (R) and absorbance (A) of sound in a membrane or frit in the presence of a blockage.

FIG. 9A illustrates schematically the transmission (T), reflectance (R) and absorbance (A) of acoustic waves/sound interacting with a porous member such as a frit in the presence of a blockage. In FIG. 9A, I represents an incident wave (arising from, for example, a speaker) to the frit (or other porous member) and $R_1$, $R_2$, and $R_3$ are the reflected waves at the surface of the frit, at the top of the frit, and at the blockage, respectively. T represents the transmitted wave and A represents the absorbed wave.

In a number of embodiments hereof, a total or combined reflected wave $R=R_1+R_2+R_3$ is measured. The following equation describes how $R_1$ relates to the incident wave: $R_1 \approx I*\Gamma_1$ where $\Gamma_1$ is the reflection coefficient of the frit to chamber border. The reflection coefficient is frequency dependent and contains phase and amplitude information. The following equation describes how $R_2$ relates to the incident wave: $R_2 \approx I*(1-\Gamma_1)*\Gamma_2$, wherein $\Gamma_2$ is the reflection coefficient of the frit to air/blockage border. Similarly, $R_3$ relates to the incident wave in the following equation: $R_3 \approx I*(1-\Gamma_1)*(1-\Gamma_2)*\Gamma_3$, wherein $\Gamma_3$ is the reflection coefficient of a blockage/environmental element spaced from the frit. The total reflected wave measured at a microphone hereof takes into account all three reflected waves.

Figure 9B:
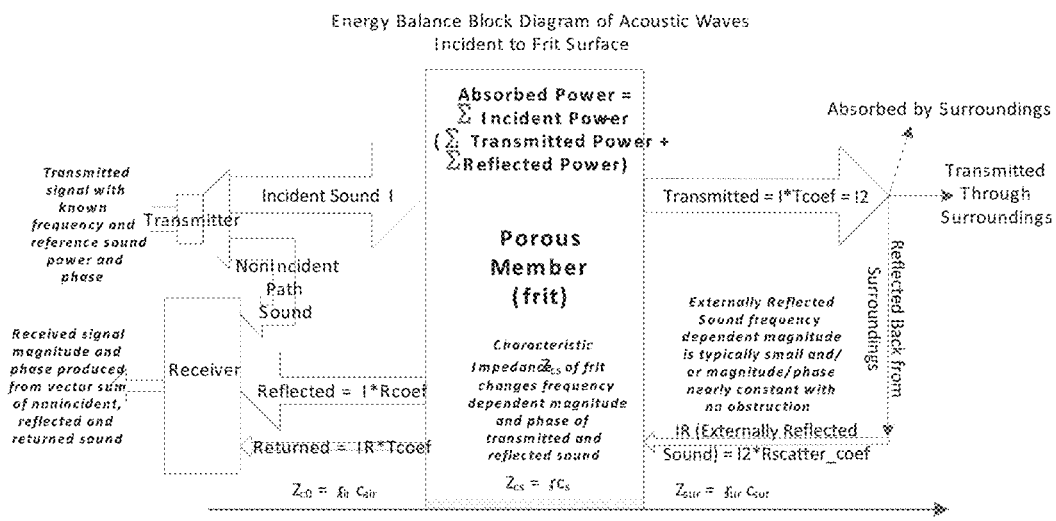
FIG. 9B illustrates an energy balance block diagram of acoustic waves incident to a porous member such as a frit.

FIG. 9B depicts another schematic illustration of an embodiment of a retroreflective acoustic interrogation system hereof to assess changes in acoustic properties of a porous member or barrier and/or changes in the acoustic reflection on the side opposite the acoustic wave source or transmitter and the acoustic wave sensor or receiver, which are indicative of the introduction or presence of an obstruction or blockage. As described above, a retroreflective system is particularly advantageous in situations where placement of the transmitter and/or receiver on opposite sides of the porous member or barrier is difficult or dangerous.

The operation of such system may be discussed using acoustic energy balance principles that dictate that the sum of the energy transmitted through, reflected from and absorbed within a closed boundary is equal to the sum of energy/power generated within and/or incident on that boundary. This principle is useful in describing the propagation of the acoustic interrogation signal generated from the acoustic wave source or transmitter back to the acoustic wave sensor or receiver. Considering separate boundaries drawn about the transmitter and receiver, the fraction of acoustic energy that is returned to the receiver from the transmitter is divided between the sum of the reflected and returned energy resultant from sound incident on the porous member and the acoustic energy that propagates to the receiver but does not impinge upon the porous member. The non-incident path acoustic energy is unmodified by the acoustic impedance of the porous member or the surroundings on the opposite side of the porous member and thus contains little to no information about these. A fraction of the acoustic energy returned to the receiver from the sound incident upon the porous member includes the vector sum of the energy reflected by the porous member and the energy that takes the circuitous path through the porous member to the surroundings on the outside of the porous member and is reflected back to the porous member and then transmitted back through the porous member to the receiver. The amplitude and phase of the reflected energy results mostly from the acoustic impedance (expressed in the reflection coefficient Rcoef) of the porous member and thus contains information primarily related to the porous member. The amplitude and phase of the acoustic energy returned from the surroundings on the outside of the porous member is impacted twice by the acoustic impedance of the porous member (expressed in transmission coefficient Tcoef) and the composite impedance of the surroundings (expressed in Rscatter_coef), and thus contains composite information about the porous member and surroundings.

Figure 9C:
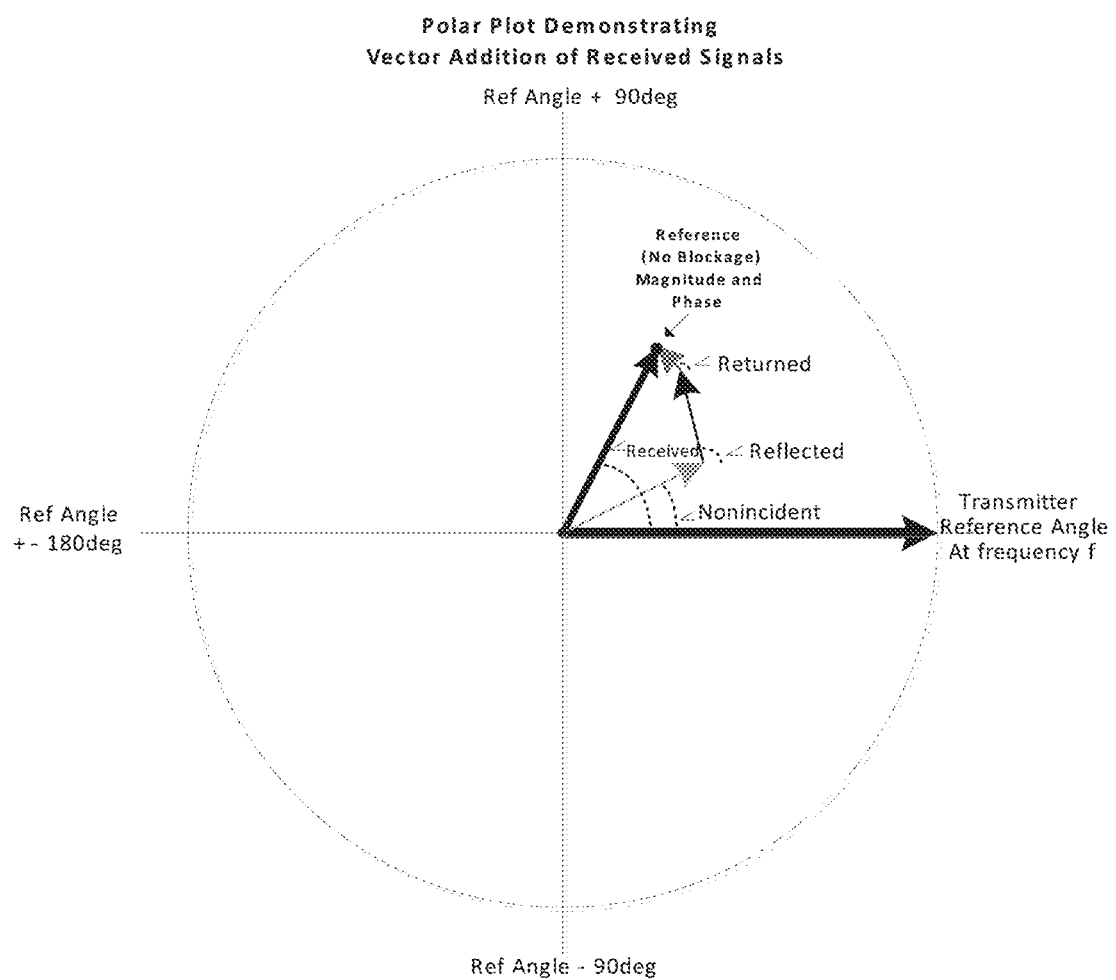
FIG. 9C illustrates a polar plot setting forth vector addition of received signals.
Figure 9D:
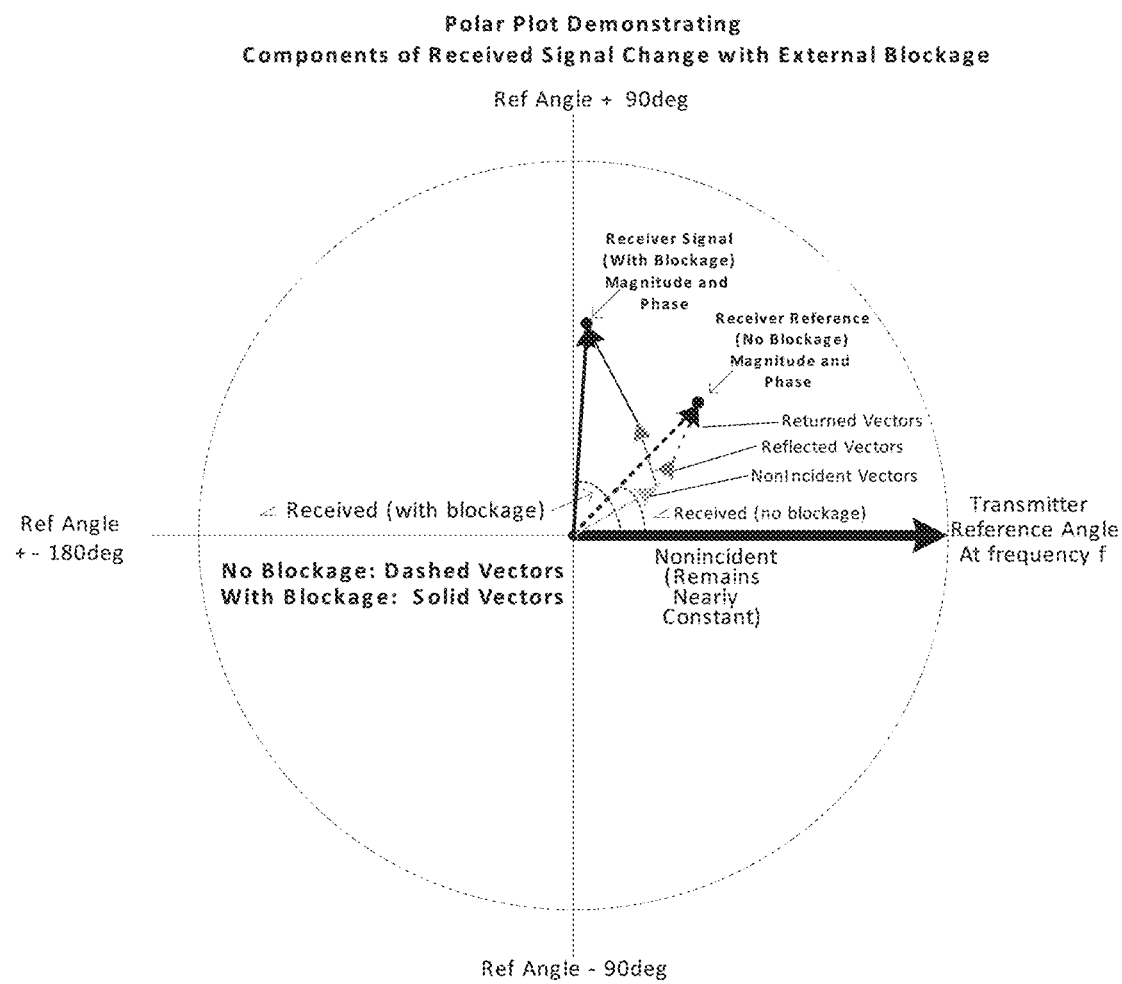
FIG. 9D illustrates a polar plot setting forth components of a received signal change in the presence of an external blockage.

FIG. 9C illustrates a graphical vector summation of the signal components returned to the receiver resulting in the composite received signal using the transmitter amplitude and phase as a reference. The magnitudes and phases of these vectors are frequency dependent and thus the composite sum results in a received signal with frequency dependent magnitude and phase. The vector components with the greatest magnitude and/or greatest phase deviation impact the magnitude and phase of the composite received signal most. As illustrated in FIG. 9D, the non-incident acoustic signal returned to the receiver is unaffected by changes in the acoustic impedance of the porous member or the surroundings beyond the porous member and therefore contains negligible information relevant to blockage detection. This suggests an acoustic design strategy that maximizes the incident fraction of transmitter power while minimizing the fraction propagating in the non-incident path to maximize the magnitude and impact of information bearing signals on the composite received signal while minimizing the impact and influence (noise) of the information deficient, non-incident signal.

The acoustic interrogation system utilizes correlation of changes in the amplitude and/or phase of the transmitter acoustic energy returned to the receiver with changes in gas permeability through the frit and/or combined frit and external obstructions to infer changes in restriction of gas transport (blockage) from external surroundings to/from the transmitter/receiver side of the frit. Because the acoustic impedance (and related transmission, reflection and absorption coefficients) of the porous member and external obstructions is frequency dependent, for the purposes of blockage detection, one may select interrogation frequencies that maximize the difference in reflection and/or returned sound amplitude and/or phase between blocked and unblocked conditions. Such frequencies are readily determined via, for example, routine experimental characterization of a porous member as described herein at, for example, the time of manufacture. The percentage of blockage can be inferred or a Boolean blocked state declared based on the magnitude and/or phase change relative to the reference magnitudes and/or phases of the unblocked system. The polar plot in FIG. 9D illustrates resultant changes in the magnitude and phase of the received signal resulting from the returned and reflected vector changes resulting from an external obstruction.

Figure 9E:
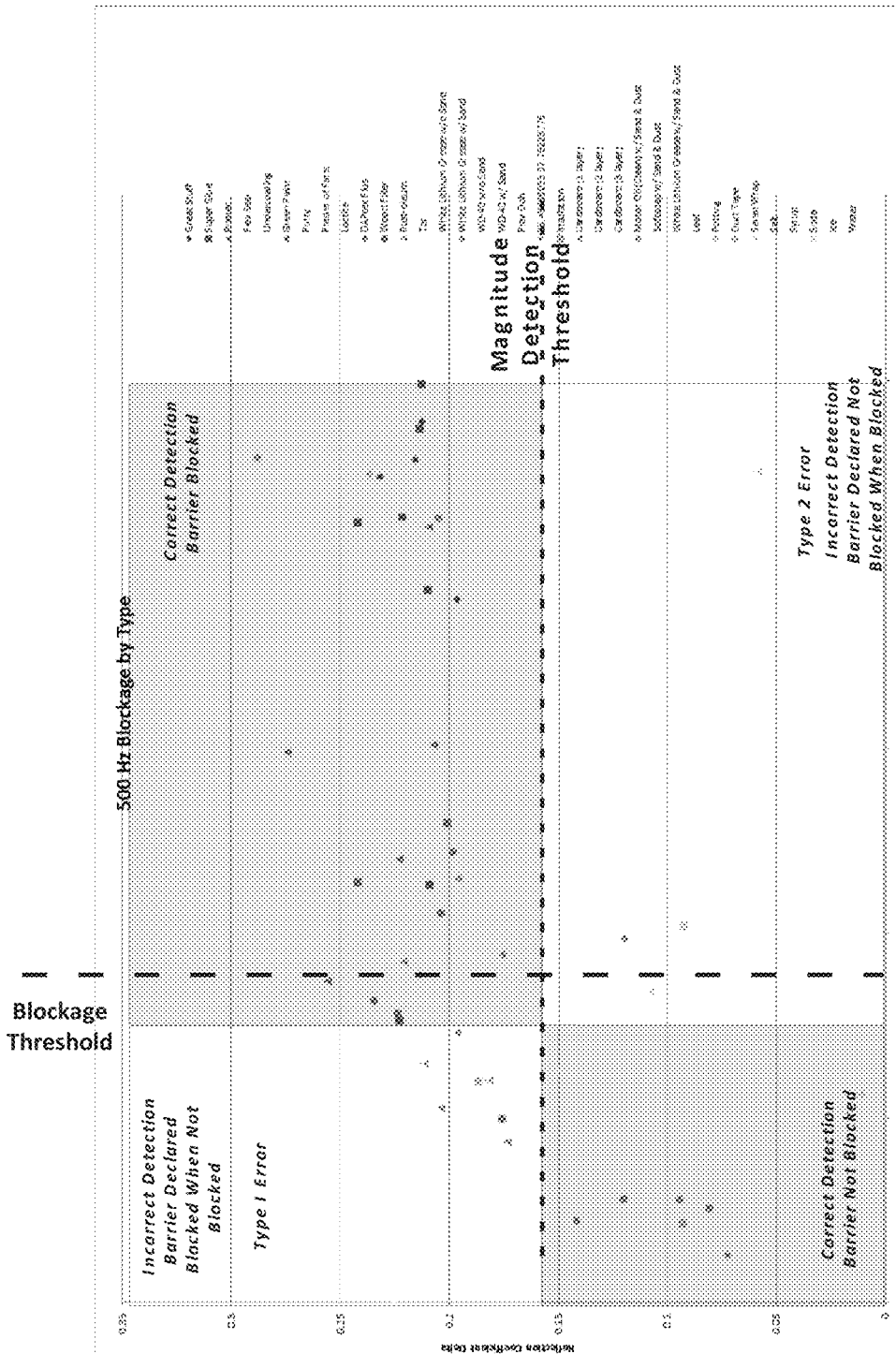
FIG. 9E illustrates a representative example of blockage classification and classification errors utilizing a single parameter (change in reflection magnitude) at a single interrogation frequency (500 Hz).

In a number of embodiments, blockage detection is significantly improved by utilizing both magnitude and phase changes of the received signal at a single or at multiple frequencies to create a multidimensional threshold scheme for discerning the blockage state of the porous member. Use of a singular threshold, for example reflection magnitude, at a single frequency can result in blockage detection errors as illustrated in FIG. 9E. Similar to FIG. 7, in FIG. 9E, the change in reflection at 500 Hz with different blockage materials applied to the porous member is plotted against the resultant measured percent blockage. The horizontal Blockage Threshold line at 30% blockage represents a detection target. In the representative example of FIG. 9E, a blockage above 30% is determined to be blocked (with, for example, an alert of an operator/operator system), while a blockage below this threshold is determined to not be blocked. In this single frequency, single threshold schema, blockage is detected using the vertical Magnitude Detection Threshold value. Changes in reflection magnitude exceeding this threshold are determined to be blocked while those falling below the threshold are determined not to be blocked. As illustrated, this singular threshold approach gives rise to detection errors as some of the blockage materials exhibit reflection magnitude changes exceeding the threshold when blockage is below 30% (Type 1 error) while some materials exhibit reflection magnitude changes falling below the detection threshold when blockage exceeds 30% (Type 2 error). It is desirable to avoid Type 1 errors as such errors could result in determination/alert of a fault and/or initiation of a maintenance cycle to clear or repair a blockage that is not significant. It is also desirable to avoid Type 2 errors as such error could lead to the failure to determine/alert of a fault for a blocked porous member (indicating that flow through the porous member is not significantly impeded) when a potentially impairing blockage exists.

Figure 9H:
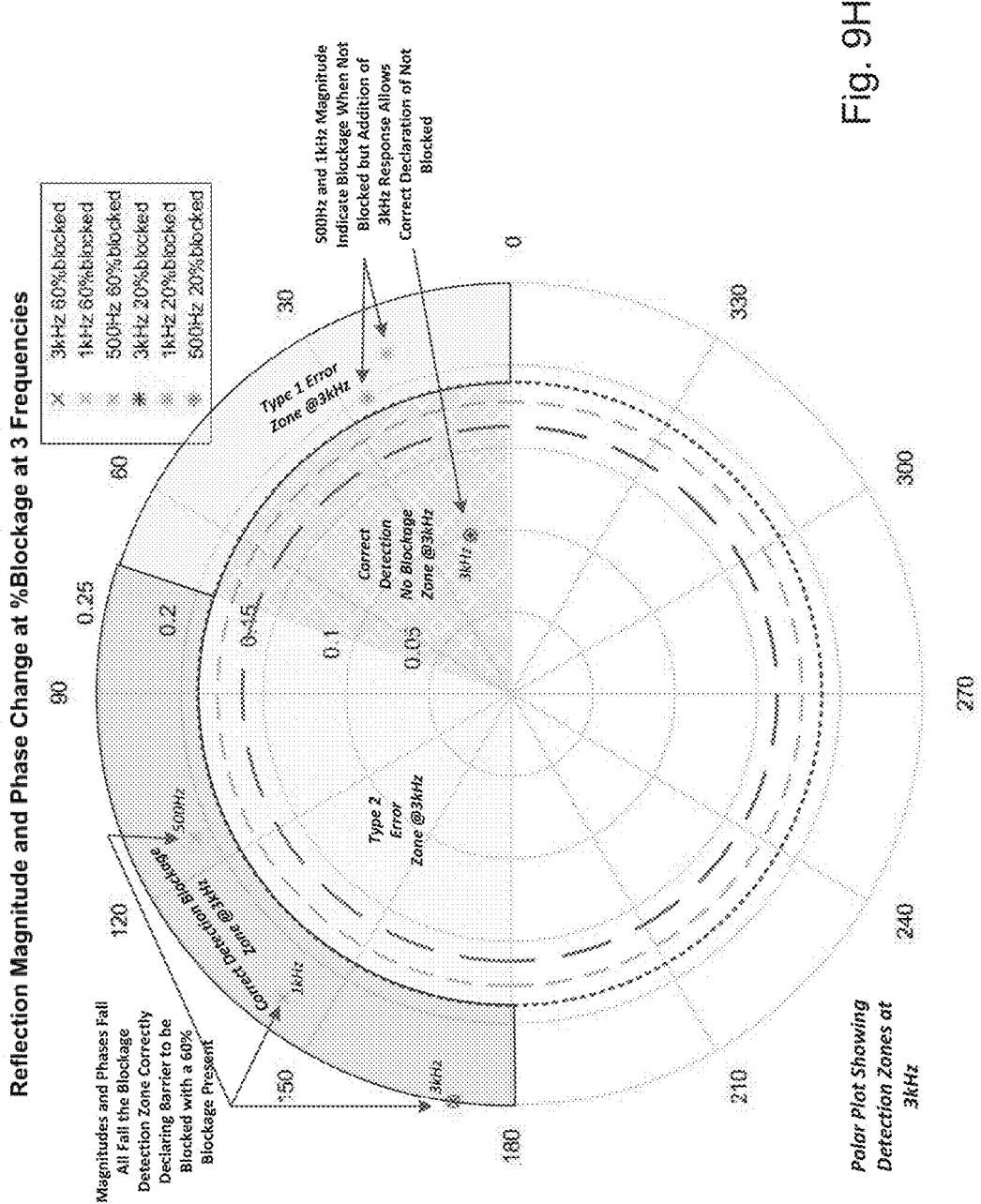
FIG. 9H illustrates a representative polar plot combining magnitude and phase at three interrogation frequencies for 20% and 60% blockage wherein the shaded areas demonstrate the application of the detection zones identified in FIG. 9E applied to the blockage detection case at 3 kHz.
Figure 9I:
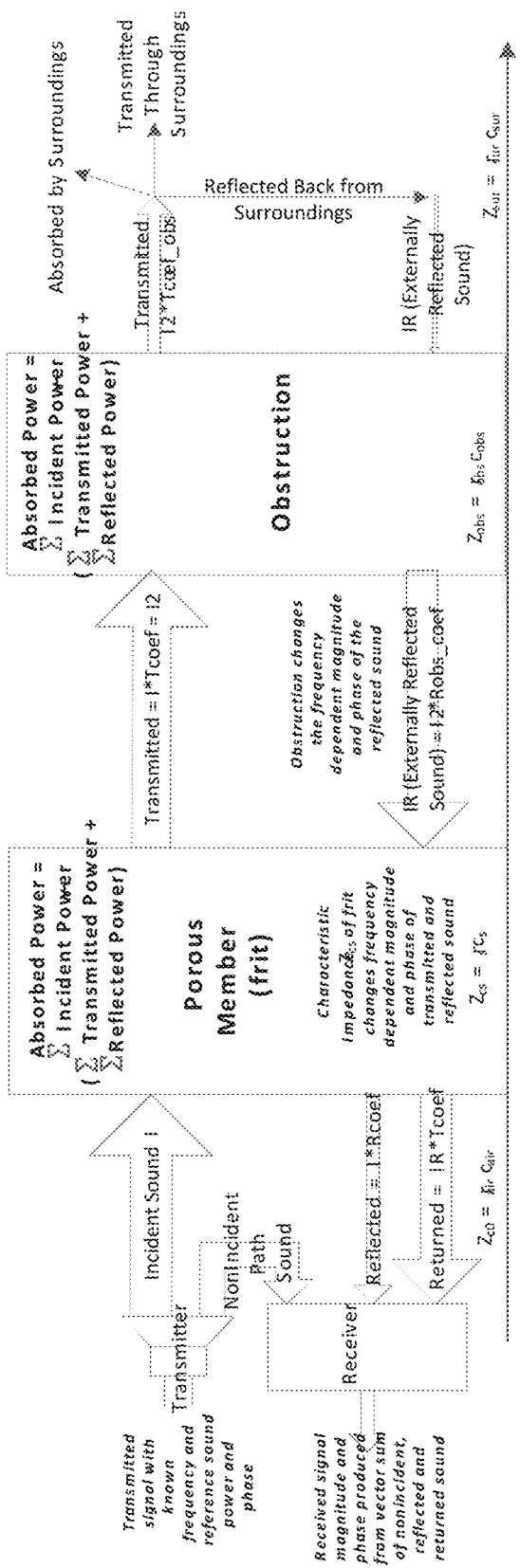
FIG. 9I illustrates a block diagram setting forth a representative embodiment of a methodology for discrimination of blockage caused by obstruction on an outside of a porous member.

FIGS. 9F through 9H illustrates the use of both magnitude and phase data from three separate interrogation frequencies to discern the difference in a 20% blockage and 60% blockage. FIGS. 9F and 9G demonstrate the change in magnitude and phase for 20% and 60% blockages with the respective thresholds at each frequency superimposed. The blockage status would have been determined/alerted incorrectly (Type 1 error) had only the magnitude responses at 500 Hz and 1 kHz been utilized in the detection. Assuming the detection scheme requires the magnitudes of all interrogation frequencies to exceed their respective magnitude thresholds to determine/alert the porous member to be blocked, the inclusion of the additional magnitude at 3 kHz would result in the correct declaration of no blockage. FIG. 9I illustrates a polar view of the combined magnitude and phase thresholding with the detection boundaries at 3 kHz superimposed to further illustrate the use of combined response thresholds to reduce false classification and declaration of the blockage state of the porous member.

Blockage discrimination assesses the source of the detected blockage (that is, an obstruction/blockage external to the porous member or an obstruction/blockage arising from internal contamination/infiltration of the pores of the porous member) by utilizing frequencies at which the composite receiver signal is dominated by either the returned signal (blockage resulting from an external obstruction) or the reflected signal (blockage resulting from porous member contamination). In the case that a blockage is sitting on the surface of a frit or other porous membrane, an operator may, for example, clean the surface of the porous. In the case that a blockage agent has infiltrated pores of a frit or other porous member, replacement is likely required.

FIG. 9I illustrates the discrimination and assessment of a blockage or obstruction adjacent to the porous member (external obstruction). To discriminate between the porous member and an external obstruction as the source of received acoustic signal change, an interrogation frequency (or frequencies) is selected that is normally, substantially transparent to the porous member (that is, frequencies where transmission through the porous member is high and porous member reflection and absorption are low) so that changes in the composite received signal are dominated by changes in the returned signal resultant from the introduction of the external blockage or obstruction.

FIG. 10A through 12C illustrates changes in the frequency dependent acoustic signal power transmitted to the surroundings, reflected/returned to the receiver and absorbed power with the introduction of an external blockage or obstruction residing beyond the outside surface of the porous membrane. As used in FIGS. 10A through 12C, "untreated" indicates the reference case of a normal, unobstructed porous member or frit, while "treated" indicates the changes resulting from addition of an external blockage or obstruction. Ra represents the composite (reflected+returned) signal to the receiver dominated by the reflection of the obstruction and subsequently, the returned vector. Ra increases with the presence of a blockage as returned power increases as a result of reflection from the blockage. Ta represents acoustic power transmitted through the combined porous member and any blockage. Ta decreases with blockage as a result of absorption and reflection. Alpha represents acoustic power absorbed by a combination of the porous member and any blockage. Alpha increases with the presence of a blockage as a result of absorption thereby. In the case of the porous metal frits studied in FIGS. 10A through 12C, a natural resonance at 6.5 kHz of the uncontaminated frit increases porous member/frit absorption and decreases frit transmission so that the composite receiver signals for the unblocked and blocked cases are essentially identical and are dominated by the reflected signal from the porous member/frit.

Figure 10A:
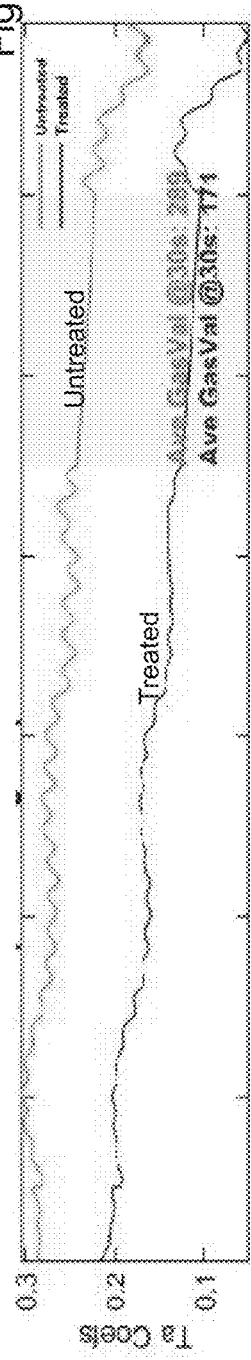
FIG. 10A illustrates transmission coefficient change in the case of duct tape blockage of the porous metal frit of the gas sensor device of FIG. 4 over a range of frequencies.
Figure 10B:
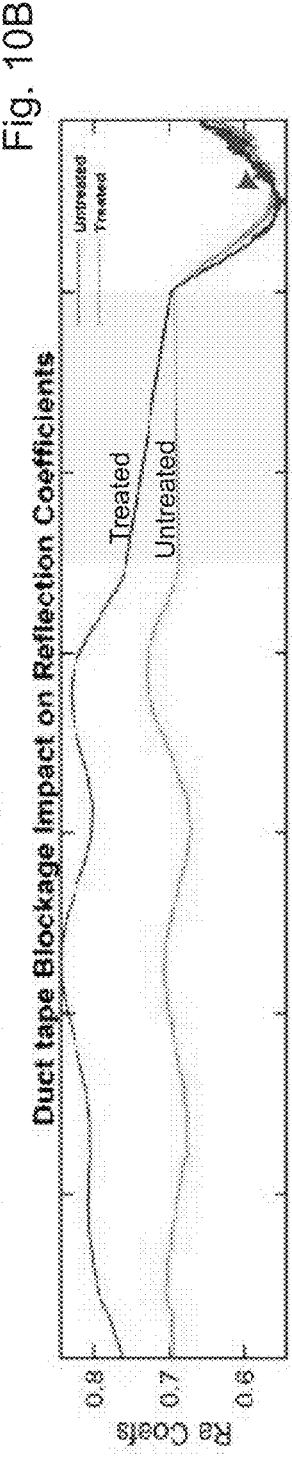
FIG. 10B illustrates reflection coefficient change in the case of duct tape blockage of the porous metal frit of the gas sensor device of FIG. 4 over a range of frequencies.
Figure 10C:
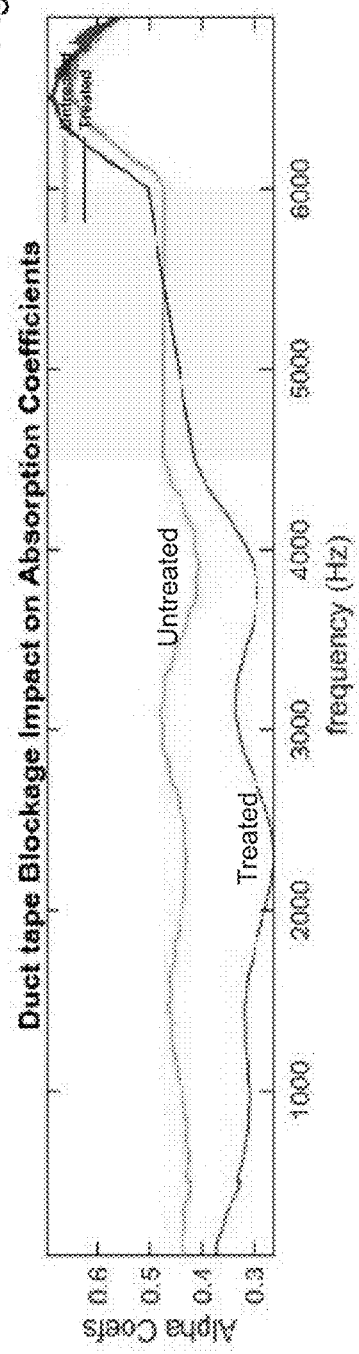
FIG. 10C illustrates absorption coefficient change in the case of duct tape blockage of the porous metal frit of the gas sensor device of FIG. 4 over a range of frequencies.
Figure 11D:
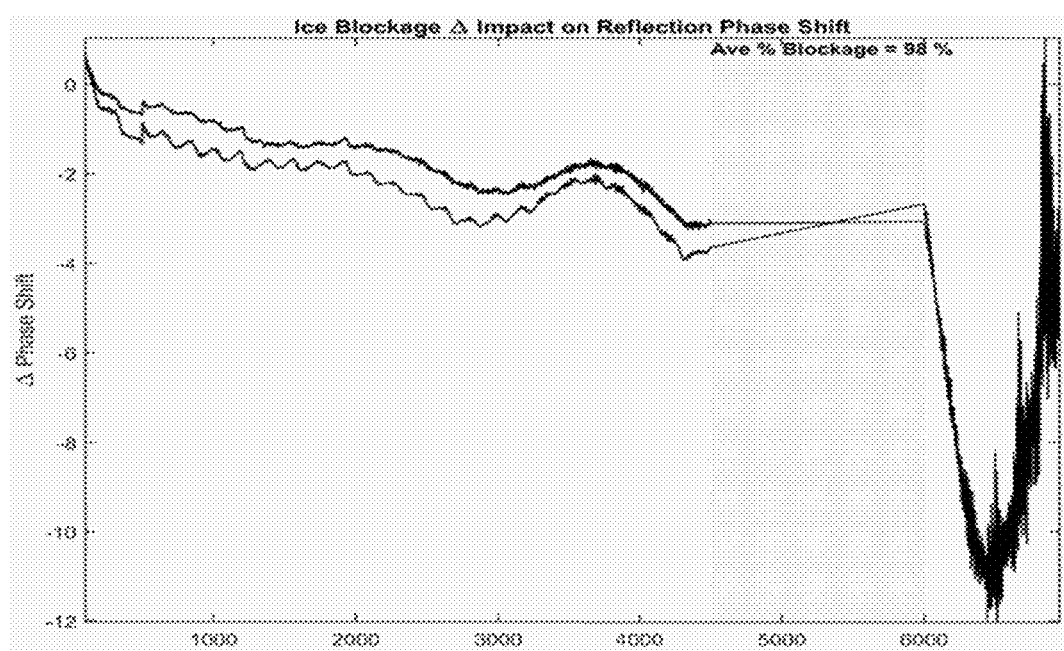
FIG. 11D illustrates a phase shift of a wave traveling through a frit which occurs in the presence of an ice blockage.

FIGS. 10A, 10B and 10C, illustrate the test system transmission coefficient, reflection coefficient and alpha/absorption coefficient output, respectively, for an untreated frit 140*b* and for frit 140*b* blocked with duct tape. FIGS. 11A, 11B and 11C illustrate the test system transmission coefficient, reflection coefficient and alpha/absorption coefficient output, respectively, for an untreated frit 140*b* and for frit 140*b* blocked with ice. FIGS. 12A, 12B and 12C illustrates the test system transmission coefficient, reflection coefficient and alpha/absorption coefficient output, respectively, for an untreated frit 140*b* and for frit 140*b* blocked with salt. In FIG. 11A through 12C, two frits 140*b* were tested in each study As illustrated in FIG. 11B, the reflection magnitude coefficient changed by approximately 20% throughout the entire frequency range tested in the ice blockage studies. The reflection magnitude coefficient output is slightly different for the frits baked with salt, in which the reflection magnitude coefficient changes by about 20% at frequencies below 1 kHz, but tapers off to having the same response as a clean frit at approximately 6.5 kHz. As described above, it was determined that at approximately 6.5 kHz, frit 140*b* is at a resonance and absorbs the sound near that frequency.

FIGS. 11A through 11C, for example, show the frequency dependency of the amplitude of each aspect of the frit, the transmission, the absorption, and the reflection. The reflection, when frit 140*b* is untreated with a blocking agent, corresponds to about 70% of the incident signal's amplitude (see, for example, FIG. 11B or 12 B). When the frit is treated with a blocking agent, the reflection coefficient can approach 100% (see, for example, FIG. 12B).

Figure 13A:
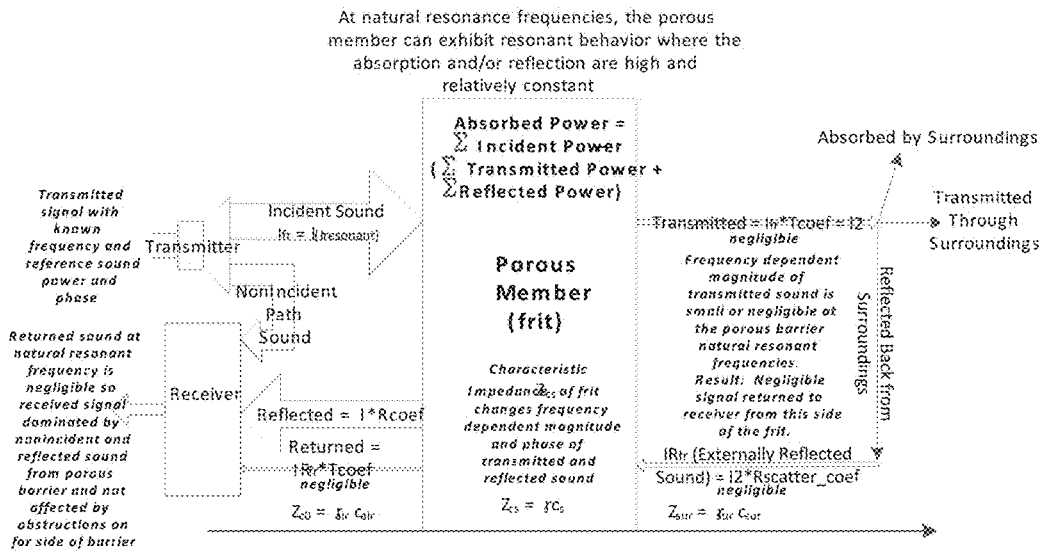
FIG. 13A illustrates a block diagram of an embodiment of a system and methodology for discrimination of acoustic changes originating from the porous member using one or more natural resonant frequencies of the porous member that block transmission wherein the porous member is unobstructed by internal contaminants.
Figure 13B:
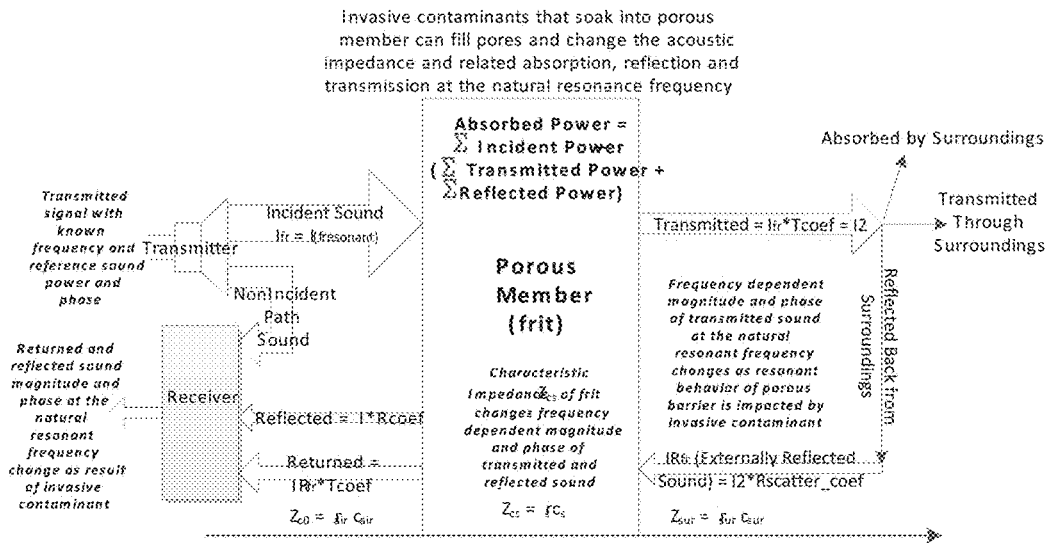
FIG. 13B illustrates a block diagram of an embodiment of a system and methodology for discrimination of acoustic changes originating from the porous member using one or more natural resonant frequencies of the porous member that block transmission showing changes in reflected and returned signal resulting from impedance changes (for example, shifts in internal resonant frequencies) resulting invasive contamination of the frit.

FIGS. 13A and 13B illustrate discrimination and assessment of acoustic changes to frit 140*b* (indicating internal contamination of a porous member such as frit 140*b*). To discriminate the porous member as the source of received acoustic signal change (inferring a potential blockage by contaminants in the porous member), an interrogation frequency or set of frequencies is selected that is normally opaque to the porous member (that is, the acoustic signal penetrating the porous member is normally absorbed rather than transmitted therethrough) and significant changes in reflected power occur between a normal and contaminated porous member. At these frequencies, the received signal is relatively unaffected by presence or absence of obstructions at the outside surface of the frit since only an insignificant amount of acoustic power is transmitted to such an external obstruction and subsequently returned to the receiver.

Figure 14:
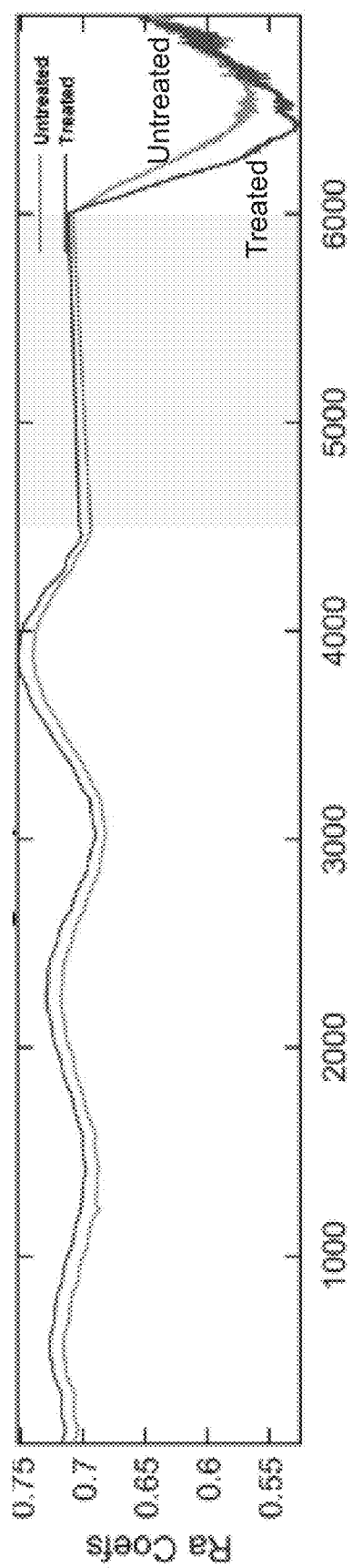
FIG. 14 illustrates the frequency dependence of the reflectance coefficient in a study showing the change in acoustic energy reflected to the receiver at a resonant frequency of approximately 6.5 kHz as a result of contamination (infiltration) of the pores of a porous member (frit).

FIG. 14 illustrates a change (reduction) in acoustic power returned to the receiver at a 6.5 kHz natural resonance frequency for frit 140b resulting from a change in the acoustic impedance of the frit 140b arising from a contaminant that has soaked into or infiltrated the pores of frit 140b. In FIG. 14 there is a significant difference at 6.5 kHz between the reflected power of the treated versus untreated response for contaminated or infiltrated frit 140b, while in the case of an external or surface obstruction as, for example, illustrated in FIG. 10B, the reflected power is largely unaffected by the external obstruction.

Figure 15A:
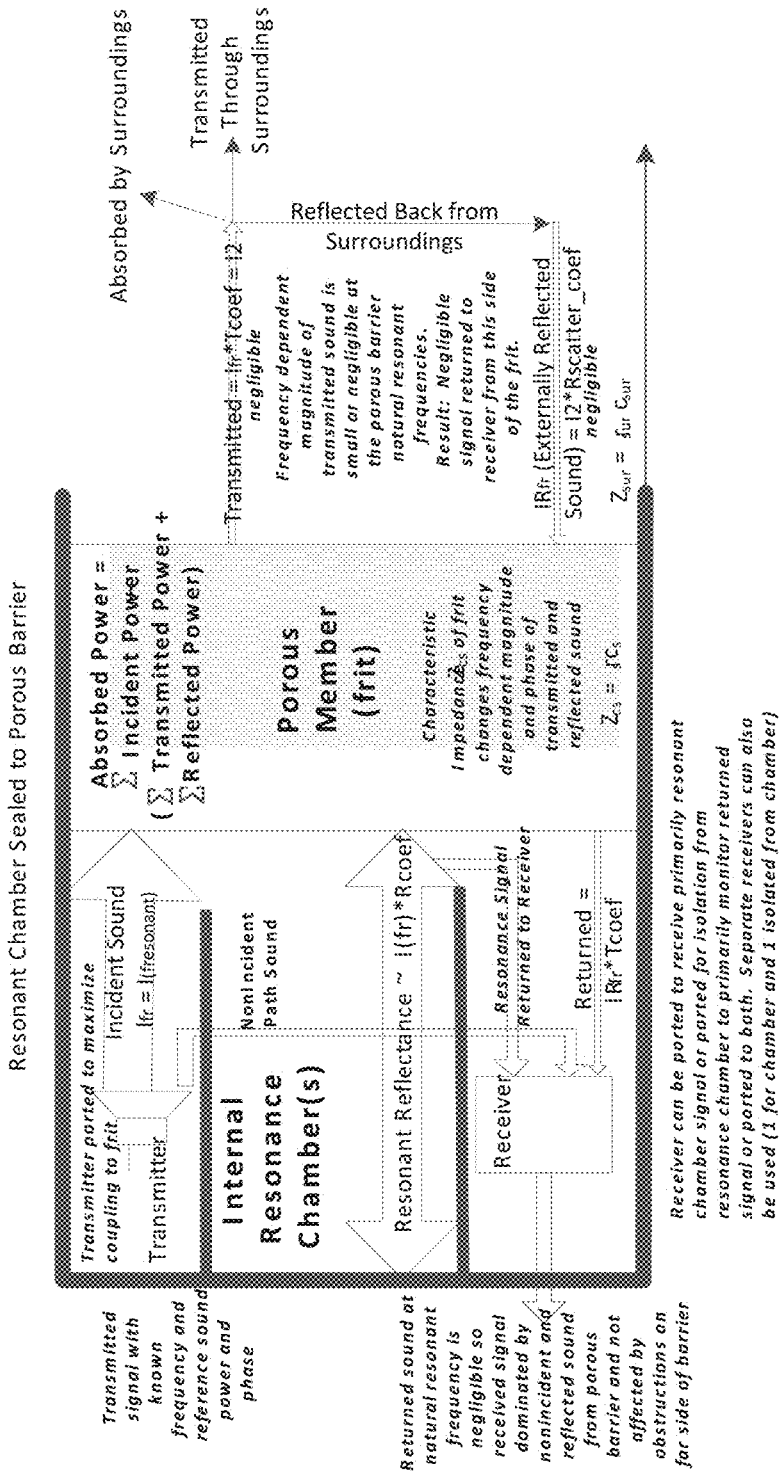
FIG. 15A illustrates a block diagram of an embodiment of a system and methodology for enhanced resonant frequency monitoring facilitated by selection of geometry of chamber coupled to the porous member and speaker/microphone port geometry using an internal resonance chamber.
Figure 15B:
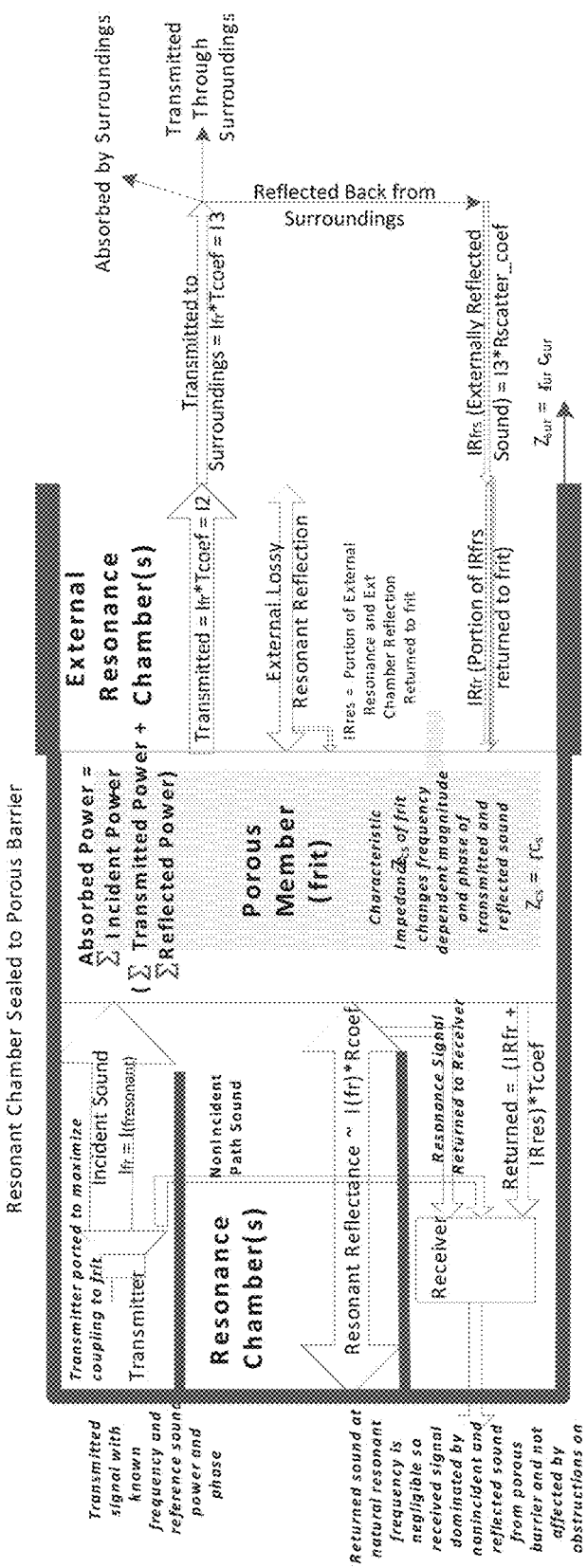
FIG. 15B illustrates a block diagram of an embodiment of a system and methodology for enhanced resonant frequency monitoring facilitated by selection of geometry of chamber coupled to the porous member and speaker/microphone port geometry with the addition of external resonance chamber.

In a number of embodiments, the detection of magnitude and/or phase changes associated with porous member resonant frequencies and/or detection of changes in the porous member resonant frequency may be enhanced through design of the geometry of the chamber coupling the speaker/microphone system to the porous member. The resonant frequency of such a system may, for example, be determined by the combined acoustic impedance of the porous member and acoustic properties of the connected chamber. Additional detection enhancement may, for example, be realized through selection of the geometry of acoustic ports connecting the speaker and/or the microphone to the chamber sealed to the porous member to achieve sympathetic resonance as depicted in FIG. 15A. Alternately or additionally, an acoustic resonant chamber may be affixed to the environmental (external) side of the porous member to enhance the signal returned to the receiver through the porous member as illustrated in FIG. 15B.

Figure 16:
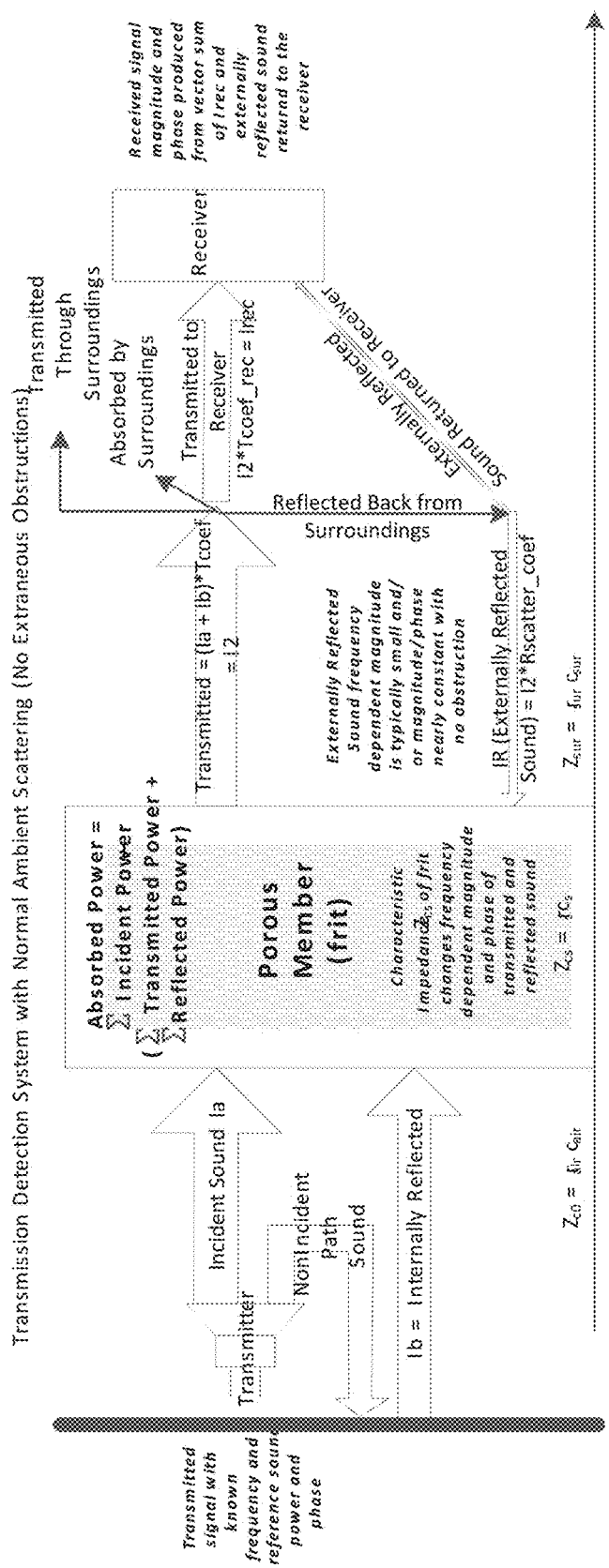
FIG. 16 illustrates a block diagram of an embodiment of a system and methodology for transmission detection of a blockage showing principal acoustic signal propagation for a non-blocked condition.
Figure 17A:
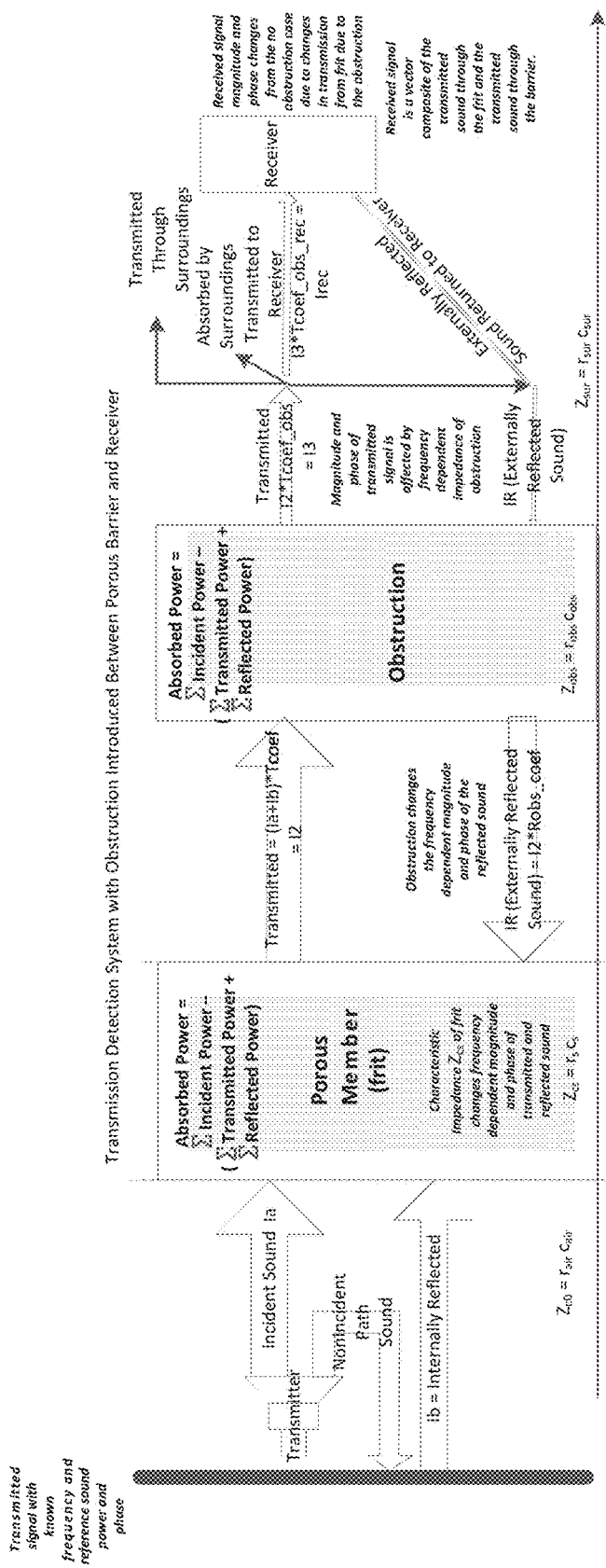
FIG. 17A illustrates a block diagram of an embodiment of a system and methodology for transmission detection of a blockage showing obstruction between the porous member and the receiver.
Figure 17B:
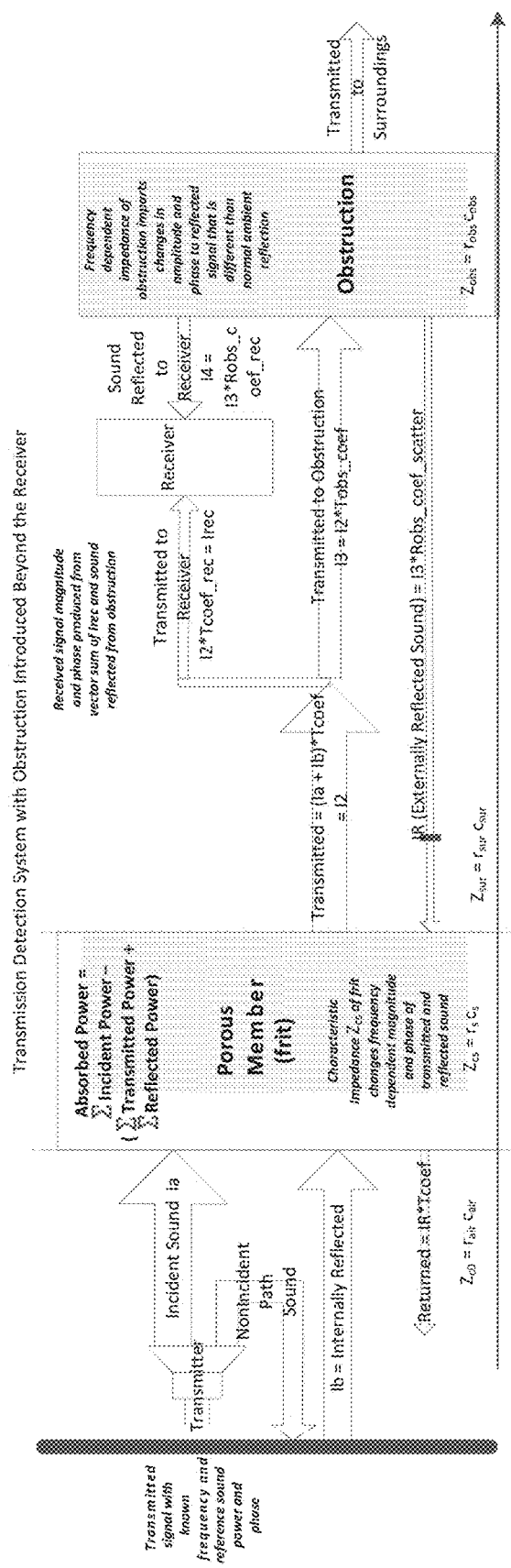
FIG. 17B illustrates a block diagram of an embodiment of a system and methodology for transmission detection of a blockage showing obstruction on an opposite side of the receiver from the porous member.

Retroreflective systems as described above offer advantages by permitting the transmitter and receiver to reside on the same side of the porous member. Once again, this arrangement is especially beneficial where the porous member is used to separate hazardous or explosive environments on one side (external) from components on the other side (internal) that can be damaged or impaired by the hazardous environment or represent a potential ignition source to the external environment. However, the detection and discrimination of porous member blockages using acoustic signal magnitude and/or phase changes is not limited to retroreflective systems. An alternative is to construct a detection system to directly monitor the acoustic signal transmitted through the porous member. FIG. 16 schematically illustrates an embodiment of such a transmission detection system using a transmitter and receiver located on opposite sides of the porous member. Such embodiments may include additional barriers or protection components/methods to protect the receiver from the external environment or to isolate the receiver as an ignition source. As described above, intrinsically safe circuitry may be used for the receiver. Added receiver barriers may present the opportunity for blockages to form on the receiver barrier and the porous member separating the sensor from the ambient environment differently, thereby complicating and potentially impacting the reliability of detection of blockages of the porous member. As depicted in FIG. 16, the detection signal includes a composite of a portion (Irec) of the acoustic signal transmitted through the porous member or barrier (I2) directly to the receiver and acoustic signals reflected and scattered to the receiver from the surroundings. Thus, blockage detections and discrimination are determined from changes in the magnitude and/or phase of the composite signal at one or more frequencies. Unlike a retroreflective system, it is possible for the blockage to reside between the porous member and the receiver or beyond the receiver as depicted in FIGS. 17A and 17B, respectively, requiring different or additional correlation between the received acoustic signal and blockages to associate changes in the detection system with changes in blockage conditions. Additionally, the discrimination of external blockage and contamination of the porous member is complicated by the possibility of blockages absorbing or reflecting at resonant frequencies of the porous member, potentially complicating detection of changes in porous member transmission as a result of contaminant induced resonance changes.

Numerous algorithms were tested on the raw data developed using devices or systems hereof such as device 100b and testing system 100b', and there are many ways to process the data that will give a signal that will change with blockage. In a number of embodiments, an algorithm was used that was based on a lock-in approach. Both the phase and amplitude of a signal played over the speaker and received by the microphone will change when a porous member becomes blocked as described above. A lock-in approach provides both of those outputs with little processing. A lock-in algorithm is, by its nature, a monotone or very narrow band detector. Detection across multiple frequencies using a single lock-in detector approach requires multiple interrogations in which the acoustic transmitter is excited one frequency at a time. Alternatively, multiple frequency interrogation can be made with the lock-in by driving the transmitter at multiple frequencies simultaneously (if such frequencies are separated sufficiently to discriminate with the lock-in detector bandwidth) and detecting with parallel lock-in detectors (one for each frequency). Multiple frequency interrogation can also be made by recording the receiver signal and repeatedly passing that signal through the lock-in detector, which is locked to each frequency of interest during each pass. Multi-tone and broad-band interrogation signals may, for example, be used with Fourier-based frequency response function detection. Other broadband compatible detection schemes may be used with broadband or multi-toned techniques. One may also use time domain detection techniques. Once again, many detection schemes are suitable for use in the devices, systems and methods hereof. Examples of suitable detection schemes include, but are not limited to, lock-in algorithms, Fourier transforms, wavelets/curvelets, and the Hilbert transform.

In a number of embodiments, an acoustic wave source or speaker can also be used as an acoustic wave sensor in devices hereof. In that regard, changes in sound pressure within the inner chamber of the housing arising from blockage of a porous member can modify the speaker's (wave source's) acoustic load resulting in distortion and/or other frequency referable changes in magnitude and/or phase detectable in changes in the back emf, current or impedance (combined emf and current) at the speaker drive terminals. Similar to utilization of signals received by a microphone or receiver separate from the transmitter as discussed elsewhere herein, such measurements and assessments of changes in the speaker acoustic load can be related to blockage of the porous member.

In addition to sensor output corrections associated with the electronic interrogation of a sensor as described above, devices and systems hereof may also be operable to or adapted to apply one or more corrections to sensor output determined as a result of the flow path/blockage test. In that regard, sensors may, for example, be thought of as "molecule counters". Analytical sensors are thus calibrated in a manner that a certain amount of analyte molecules react at the analytical working or sensing electrode(s) as they diffuse through the instrument and measured values are converted to, for example, a part per million (ppm) or percentage based equivalent readings based upon previous calibration. When a porous member or barrier associated with a sensor inlet is open and unobstructed, rates of diffusion are very repeatable under the same conditions. As a porous member becomes blocked or flow paths are otherwise obstructed, the rate at which the molecules can diffuse from outside the instrument housing to the sensor can slow, thus lowering the rate at which molecules will encounter the active portion of the sensor, and thereby lowering the output. By measuring partial blockages as a result of one or more tests hereof, one can adjust the sensitivity of the sensor to maintain accurate readings regardless of such partial blockages.

Percent blockage may, for example, be readily experimentally correlated with a correction factor. An associated lookup table or an associated algorithm/formula may, for example, be stored in memory of the devise and systems hereof, and a correction factor for sensor sensitivity may be determined therefrom.

The foregoing description and accompanying drawings set forth a number of representative embodiments at the present time. Various modifications, additions and alternative designs will, of course, become apparent to those skilled in the art in light of the foregoing teachings without departing from the scope hereof, which is indicated by the following claims rather than by the foregoing description. All changes and variations that fall within the meaning and range of equivalency of the claims are to be embraced within their scope.

What is claimed is:

1. A method of detecting a state of blockage in a porous member separating an inner chamber of a device comprising a gas sensor responsive to an analyte positioned within the inner chamber and an ambient environment from which the analyte gas transports through the porous member to reach the gas sensor responsive to the analyte gas, comprising:

emitting pressure waves within the inner chamber via a source of pressure waves positioned within the inner chamber and spaced from the porous member so that any pressure waves emitted from the source of pressure waves that are transmitted out of the inner chamber are transmitted through the porous member, measuring a change in phase of a response via a sensor responsive to pressure waves, which is different from the gas sensor, and relating the change in phase of the response to the state of blockage in the porous member, wherein a blockage of the porous member inhibits transport of analyte gas therethrough.

2. The method of claim 1 wherein the change in phase of the response is measured via the sensor responsive to pressure waves which is positioned within the inner chamber.

3. The method of claim 1 further comprising measuring a change in magnitude of the response.

4. The method of claim 1 wherein the change in phase of the response is measured at more than one frequency.

5. The method of claim 1 wherein the change in phase and a change in magnitude of the response are measured at more than one frequency.

6. The method of claim 5 wherein measuring the response comprises measuring at least pressure waves reflected off the porous member.

7. The method of claim 6 wherein a lock-in algorithm is used to measure each of the change in amplitude and the change in phase.

8. The method of claim 5 wherein at least one of the more than one frequency is a self-resonant frequency of the porous member and a response measured at the at least one of the more than one frequency is associable with a blockage that infiltrates pores of the porous membrane.

9. The method of claim 5 further comprising using the measured response to discriminate between at least a partial blockage associated with an outside surface of the porous member and at least a partial blockage infiltrating pores of the porous member.

10. The method of claim 9 wherein pressure waves are emitted at a self-resonant frequency of the porous member and a response measured at the self-resonant frequency is associated with a determination of the at least a partial blockage infiltrating pores of the porous membrane.

11. A method of detecting a state of blockage in a porous member separating an inner chamber of a device comprising a gas sensor responsive to an analyte gas positioned within the inner chamber and an ambient environment from which the analyte gas transports through the porous member to reach the gas sensor responsive to the analyte gas, comprising:

emitting pressure waves within the inner chamber via a source of pressure waves positioned within the inner chamber and spaced from the porous member so that any pressure waves emitted from the source of pressure waves that are transmitted out of the inner chamber are transmitted through the porous member; measuring a change in a response at more than one frequency via a sensor responsive to pressure waves, which is different from the gas sensor, and relating the change in the response at more than one frequency to the state of blockage in the porous member, wherein a blockage of the porous member inhibits transport of analyte gas therethrough.

12. The method of claim 11 wherein the change in the response is measured via the sensor responsive to pressure waves which is positioned within the inner chamber.

13. The method of claim 11 wherein a change in phase of the response is measured at each frequency.

14. The method of claim 11 wherein a change in magnitude of the response is measured at each frequency.

15. The method of claim 11 wherein a change in phase and a change in magnitude of the response are measured at each frequency.

16. The method of claim 15 wherein measuring the response comprises measuring at least one of transmission, reflection or absorbance.

17. The method of claim 16 wherein a lock-in algorithm is used to measure each of the change in amplitude and the change in phase.

18. The method of claim 11 wherein at least one of the more than one frequency is a self-resonant frequency of the porous member and a response measured at the at least one of the more than one frequency is associable with a blockage that infiltrates pores of the porous membrane.

* * * * *

UNITED STATES PATENT AND TRADEMARK OFFICE
CERTIFICATE OF CORRECTION

PATENT NO. : 10,788,458 B2  
APPLICATION NO. : 15/394566  
DATED : September 29, 2020  
INVENTOR(S) : Jerin Miller et al.

Page 1 of 1

It is certified that error appears in the above-identified patent and that said Letters Patent is hereby corrected as shown below:

In the Drawings  
Sheet 3, Fig. 4, delete the reference number "13b" and insert --134b--.  
In the Specification  
Column 11, Line 6, delete "device 10" and insert --device 100--.  
Column 11, Line 30, delete "130" and insert --120--.  
Column 12, Line 29, delete "160" and insert --160b--.

Signed and Sealed this  
Fifth Day of January, 2021

Andrei Iancu  
*Director of the United States Patent and Trademark Office*